US009481647B2

(12) United States Patent
Krzyzaniak et al.

(10) Patent No.: US 9,481,647 B2
(45) Date of Patent: Nov. 1, 2016

(54) **FORMS OF [R-(R\*,R\*)]-2-(4-FLUOROPHENYL)-β, δ-DIHYDROXY-5-(1-METHYLETHYL)-3-PHENYL-4-[(PHENYLAMINO)CARBONYL]-1H-PYRROLE-1-HEPTANOIC ACID CALCIUM SALT (2:1)**

(71) Applicant: Warner-Lambert Company LLC, New York, NY (US)

(72) Inventors: Joseph Francis Krzyzaniak, Pawcatuck, CT (US); Kevin Quackenbush, Groton, CT (US)

(73) Assignee: Warner-Lambert Company LLC, New York, NY (US)

( * ) Notice: Subject to any disclaimer, the term of this patent is extended or adjusted under 35 U.S.C. 154(b) by 0 days.

(21) Appl. No.: 14/924,011

(22) Filed: Oct. 27, 2015

(65) Prior Publication Data

US 2016/0046575 A1    Feb. 18, 2016

Related U.S. Application Data

(62) Division of application No. 14/520,742, filed on Oct. 22, 2014, now Pat. No. 9,199,932, which is a division of application No. 14/021,151, filed on Sep. 9, 2013, now Pat. No. 8,895,758, which is a division of application No. 13/214,559, filed on Aug. 22, 2011, now Pat. No. 8,563,750, which is a division of application No. 11/572,333, filed as application No. PCT/IB2005/002181 on Jul. 11, 2005, now Pat. No. 8,026,376.

(60) Provisional application No. 60/589,485, filed on Jul. 20, 2004.

(51) Int. Cl.
C07D 207/00    (2006.01)
C07D 207/34    (2006.01)

(52) U.S. Cl.
CPC .................. C07D 207/34 (2013.01)

(58) Field of Classification Search
USPC ......................................................... 548/537
See application file for complete search history.

(56) References Cited

U.S. PATENT DOCUMENTS

| | | |
|---|---|---|
| 4,681,893 A | 7/1987 | Roth |
| 5,003,080 A | 3/1991 | Butler et al. |
| 5,097,045 A | 3/1992 | Butler et al. |
| 5,103,024 A | 4/1992 | Millar et al. |
| 5,124,482 A | 6/1992 | Butler et al. |
| 5,149,837 A | 9/1992 | Butler et al. |
| 5,155,251 A | 10/1992 | Butler et al. |
| 5,216,174 A | 6/1993 | Butler et al. |
| 5,245,247 A | 9/1993 | Hosogi et al. |
| 5,248,793 A | 9/1993 | Millar et al. |
| 5,273,995 A | 12/1993 | Roth |
| 5,280,126 A | 1/1994 | Butler et al. |
| 5,298,627 A | 3/1994 | Butler et al. |
| 5,342,952 A | 8/1994 | Butler et al. |
| 5,397,792 A | 3/1995 | Butler et al. |
| 5,446,054 A | 8/1995 | Butler et al. |
| 5,470,981 A | 11/1995 | Butler et al. |
| 5,489,690 A | 2/1996 | Butler et al. |
| 5,489,691 A | 2/1996 | Butler et al. |
| 5,510,488 A | 4/1996 | Butler et al. |
| 5,686,104 A | 11/1997 | Mills et al. |
| 5,969,156 A | 10/1999 | Briggs et al. |
| 5,998,633 A | 12/1999 | Jacks et al. |
| 6,087,511 A | 7/2000 | Lin et al. |
| 6,121,461 A | 9/2000 | McKenzie |
| 6,126,971 A | 10/2000 | Mills et al. |
| 6,433,213 B1 | 8/2002 | Bosch et al. |
| 6,476,235 B2 | 11/2002 | Butler et al. |
| 6,528,660 B1 | 3/2003 | Kumar et al. |
| 6,605,729 B1 | 8/2003 | Byrn et al. |
| 6,613,916 B2 | 9/2003 | Pflaum |
| 6,750,353 B2 | 6/2004 | Sorsak |
| 6,867,306 B2 | 3/2005 | Srinath |
| 7,030,151 B2 | 4/2006 | Kerc |
| 7,132,570 B2 | 11/2006 | Neckebrock et al. |
| 7,151,183 B2 | 12/2006 | Tessler et al. |
| 7,161,012 B2 | 1/2007 | Tessler et al. |

(Continued)

FOREIGN PATENT DOCUMENTS

| | | |
|---|---|---|
| WO | 9703958 | 2/1997 |
| WO | 9703959 | 2/1997 |
| WO | 0128999 | 4/2001 |
| WO | 0136384 | 5/2001 |
| WO | 0241834 | 5/2002 |
| WO | 0243667 | 6/2002 |
| WO | 0243732 | 6/2002 |
| WO | 02051804 | 7/2002 |
| WO | 02057228 | 7/2002 |
| WO | 02083637 | 10/2002 |
| WO | 02083638 | 10/2002 |
| WO | 03004470 | 1/2003 |
| WO | 03011826 | 2/2003 |
| WO | 03050085 | 6/2003 |
| WO | 03070702 | 8/2003 |
| WO | 2004022053 | 3/2004 |
| WO | 2004050618 | 6/2004 |
| WO | 2005090301 | 9/2005 |

OTHER PUBLICATIONS

Konno, T., et al., "Physcial and Chemical Changes of Medicinals in Mixtures with Absorbents in the Solid State. IV. Study on Reduced-Pressure Mixing for Practical Use of Amorphous Mixtures of Flufenamic Acid", Chem. Pharm. Bull., vol. 38, No. 7, pp. 2003-2007 (1990).
Hancock, B., et al., "Comparison of the mechanical properties of the crystalline and amorphous forms of a drug substance", Internaltional Journal of Pharmaceutics, vol. 241, pp. 73-85, (2002).
Hiestand, H. E. N., et al., "Indices of Tableting Performance", Powder Technology, vol. 38, pp. 145-159 (1984).

Primary Examiner — Rei-Tsang Shiao
(74) Attorney, Agent, or Firm — Francis J. Tinney

(57) ABSTRACT

Novel forms of [R—(R\*,R\*)]-2-(4-fluorophenyl)-β,δ-dihydroxy-5-(1-methylethyl)-3-phenyl-4-[(phenylamino)carbonyl]-1H-pyrrole-1-heptanoic acid hemi calcium salt designated Form XX, Form XXI, Form XXII, Form XXIII, Form XXIV, Form XXV, Form XXVI, Form XXVII, Form XXVIII, Form XXIX, and Form XXX, characterized by their X-ray powder diffraction, solid-state NMR, and/or Raman spectroscopy are described, as well as methods for the preparation and pharmaceutical composition of the same, which are useful as agents for treating hyperlipidemia, hypercholesterolemia, osteoporosis, benign prostatic hyperplasia (BPH) and Alzheimer's disease.

3 Claims, 24 Drawing Sheets

(56) References Cited

U.S. PATENT DOCUMENTS

| | | |
|---|---|---|
| 7,405,323 B2 | 7/2008 | Broquaire et al. |
| 8,563,750 B2 | 10/2013 | Park et al. |
| 8,895,758 B2 | 11/2014 | Krzyzaniak et al. |
| 9,199,932 B2 * | 12/2015 | Krzyzaniak .......... C07D 207/34 |
| 2003/0114686 A1 | 6/2003 | Van Der Schaaf et al. |
| 2006/0122403 A1 | 6/2006 | Suri et al. |

* cited by examiner

Raman shift (cm$^{-1}$)

Raman shift (cm$^{-1}$)

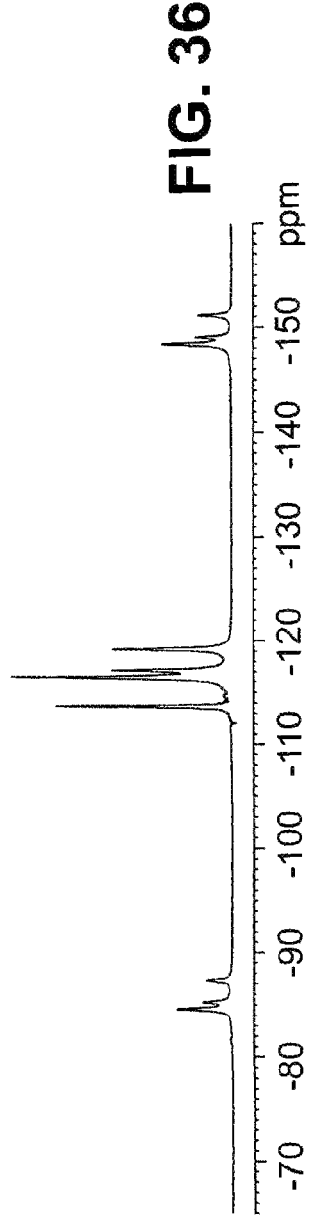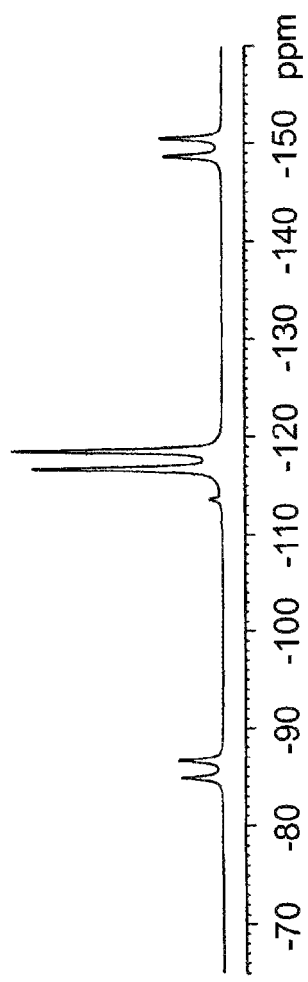

FORMS OF [R-(R*,R*)]-2-(4-FLUOROPHENYL)-β,δ-DIHYDROXY-5-(1-METHYLETHYL)-3-PHENYL-4-[(PHENYLAMINO)CARBONYL]-1H-PYRROLE-1-HEPTANOIC ACID CALCIUM SALT (2:1)

This application is a divisional application U.S. Ser. No. 14/520,742 filed Oct. 22, 2014, now pending which is a divisional application of U.S. Ser. No. 14/021,151 filed Sep. 9, 2013, now U.S. Pat. No. 8,895,758 which is a divisional application of U.S. Ser. No. 13/214,559 filed Aug. 22, 2011, now U.S. Pat. No. 8,563,750 which is a divisional application of U.S. Ser. No. 11/572,333 filed on Aug. 19, 2008, now U.S. Pat. No. 8,026,376 which is a 371 application of PCT/IB2005/002181 filed on Jul. 11, 2005, which claims benefit of provisional application U.S. Ser. No. 60/589,485 filed on Jul. 20, 2004, all of which are incorporated herein by reference in their entirety.

FIELD OF THE INVENTION

The present invention relates to novel forms of atorvastatin calcium which is known by the chemical name [R—(R*,R*)]-2-(4-fluorophenyl)-β,δ-dihydroxy-5-(1-methylethyl)-3-phenyl-4-[(phenylamino)carbonyl]-1H-pyrrole-1-heptanoic acid calcium salt useful as pharmaceutical agents, to methods for their production and isolation, to pharmaceutical compositions which include these compounds and a pharmaceutically acceptable carrier, as well as methods of using such compositions to treat subjects, including human subjects, suffering from hyperlipidemia, hypercholesterolemia, osteoporosis, benign prostatic hyperplasia, and Alzheimer's disease.

BACKGROUND OF THE INVENTION

The conversion of 3-hydroxy-3-methylglutaryl-coenzyme A (HMG-CoA) to mevalonate is an early and rate-limiting step in the cholesterol biosynthetic pathway. This step is catalyzed by the enzyme HMG-CoA reductase. Statins inhibit HMG-CoA reductase from catalyzing this conversion. As such, statins are collectively potent lipid lowering agents.

Atorvastatin calcium, disclosed in U.S. Pat. No. 5,273,995, which is incorporated herein by reference, is currently sold as Lipitor® having the chemical name [R—(R*,R*)]-2-(4-fluorophenyl)-β,δ-dihydroxy-5-(1-methylethyl)-3-phenyl-4-[(phenylamino)carbonyl]-1H-pyrrole-1-heptanoic acid calcium salt (2:1) trihydrate and the formula

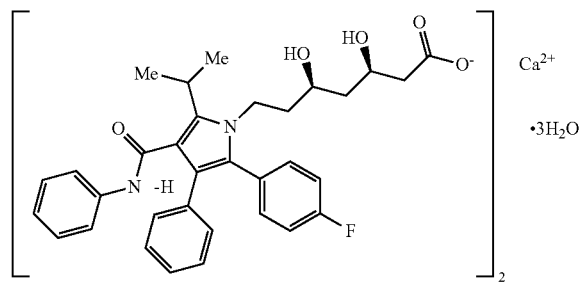

Atorvastatin calcium is a selective, competitive inhibitor of HMG-CoA reductase. As such, atorvastatin calcium is a potent lipid lowering compound and is thus useful as a hypolipidemic and/or hypocholesterolemic agent.

A number of patents have issued disclosing atorvastatin, formulations of atorvastatin, as well as processes and key intermediates for preparing atorvastatin. These include: U.S. Pat. Nos. 4,681,893; 5,273,995; 5,003,080; 5,097,045; 5,103,024; 5,124,482; 5,149,837; 5,155,251; 5,216,174; 5,245,047; 5,248,793; 5,280,126; 5,397,792; 5,342,952; 5,298,627; 5,446,054; 5,470,981; 5,489,690; 5,489,691; 5,510,488; 5,686,104; 5,998,633; 6,087,511; 6,126,971; 6,433,213; and 6,476,235, which are herein incorporated by reference.

Additionally, a number of published International Patent Applications and patents have disclosed crystalline forms of atorvastatin, as well as processes for preparing amorphous atorvastatin. These include: U.S. Pat. No. 5,969,156; U.S. Pat. No. 6,121,461; U.S. Pat. No. 6,605,729; WO 00/71116; WO 01/28999; WO 01/36384; WO 01/42209; WO 02/41834; WO 02/43667; WO 02/43732; WO 02/051804; WO 02/057228; WO 02/057229; WO 02/057274; WO 02/059087; WO 02/072073; WO 02/083637; WO 02/083638; WO 03/050085; WO 03/070702; and WO 04/022053.

Atorvastatin is prepared as its calcium salt, i.e., [R—(R*,R*)]-2-(4-fluorophenyl)-β,δ-dihydroxy-5-(1-methylethyl)-3-phenyl-4-[(phenylamino)-carbonyl]-1H-pyrrole-1-heptanoic acid calcium salt (2:1). The calcium salt is desirable, since it enables atorvastatin to be conveniently formulated in, for example, tablets, capsules, lozenges, powders, and the like for oral administration.

The process by which atorvastatin calcium is produced needs to be one which is amenable to large-scale production. Additionally, it is desirable that the product should be in a form that is readily filterable and easily dried. Finally, it is economically desirable that the product be stable for extended periods of time without the need for specialized storage conditions.

Furthermore, it has been disclosed that the amorphous forms in a number of drugs exhibit different dissolution characteristics, and in some cases different bioavailability patterns compared to the crystalline forms (Konno T., Chem. Pharm. Bull., 1990; 38; 2003-2007). For some therapeutic indications, one bioavailability pattern may be favored over another.

In the course of drug development, it is generally assumed to be important to discover the most stable crystalline form of the drug. This most stable crystalline form is the form which is likely to have the best chemical stability, and thus the longest shelf-life in a formulation. However, it is also advantageous to have multiple forms of a drug, e.g. salts, hydrates, polymorphs, crystalline, and noncrystalline forms. There is no one ideal physical form of a drug because different physical forms provide different advantages. The search for the most stable form and for such other forms is arduous and the outcome is unpredictable.

The successful development of a drug requires that it meet certain requirements to be a therapeutically effective treatment for patients. These requirements fall into two categories: (1) requirements for successful manufacture of dosage forms, and (2) requirements for successful drug delivery and disposition after the drug formulation has been administered to the patient.

There are many kinds of drug formulations for administration by various routes, and the optimum drug form for different formulations is likely to be different. As mentioned above, a drug formulation must have sufficient shelf-life to allow successful distribution to patients in need of treatment. In addition, a drug formulation must provide the drug in a form which will dissolve in the patient's gastrointestinal tract when orally dosed. For oral dosing in an immediate release dosage form, such as an immediate release tablet, capsule, suspension, or sachet, it is generally desirable to have a drug salt or drug form which has high solubility, in order to assure complete dissolution of the dose and optimal bioavailability. For some drugs, particularly low solubility drugs or poorly wetting drugs, it may be advantageous to utilize a noncrystalline drug form, which will generally have a higher initial solubility than a crystalline form when administered into the gastrointestinal tract. A noncrystalline form of a drug is frequently less chemically stable than a crystalline form. Thus, it is advantageous to identify noncrystalline drug forms which are sufficiently chemically stable to provide a practical product which is stable enough to maintain its potency for enough time to permit dosage form manufacture, packaging, storage, and distribution to patients around the world.

On the other hand, there are dosage forms which operate better if the drug form is less soluble. For example, a chewable tablet or a suspension or a sachet dosage form exposes the tongue to the drug directly. For such dosage forms, it is desirable to minimize the solubility of the drug in the mouth, in order to keep a portion of the drug in the solid state, minimizing bad taste. For such dosage forms, it is often desirable to use a low solubility salt or crystalline form.

For controlled release oral or injectable, e.g. subcutaneous or intramuscular, dosage forms, the desired drug solubility is a complex function of delivery route, dose, dosage form design, and desired duration of release. For a drug which has high solubility, it may be desirable to utilize a lower solubility crystalline salt or polymorph for a controlled release dosage form, to aid in achievement of slow release through slow dissolution. For a drug which has low solubility, it may be necessary to utilize a higher solubility crystalline salt or polymorph, or a noncrystalline form, in order to achieve a sufficient dissolution rate to support the desired drug release rate from the controlled release dosage form.

In soft gelatin capsule dosage forms ("soft-gels"), the drug is dissolved in a small quantity of a solvent or vehicle such as a triglyceride oil or polyethylene glycol, and encapsulated in a gelatin capsule. An optimal drug form for this dosage form is one which has a high solubility in an appropriate soft-gel vehicle. In general, a drug form which is more soluble in a triglyceride oil will be less soluble in water. Identification of an appropriate drug form for a soft-gel dosage form requires study of various salts, polymorphs, crystalline, and noncrystalline forms.

Thus, it can be seen that the desired solubility of a drug form depends on the intended use, and not all drug forms are equivalent.

For a drug form to be practically useful for human or animal therapy, it is desirable that the drug form exhibit minimal hygroscopicity. Dosage forms containing highly hygroscopic drugs require protective packaging, and may exhibit altered dissolution if stored in a humid environment. Thus, it is desirable to identify nonhygroscopic crystalline salts and polymorphs of a drug. If a drug is noncrystalline, or if a noncrystalline form is desired to improve solubility and dissolution rate, then it is desirable to identify a noncrystalline salt or form which has a low hygroscopicity relative to other noncrystalline salts or forms.

A drug, crystalline or noncrystalline, may exist in an anhydrous form, or as a hydrate or solvate or hydrate/solvate. The hydration state and solvation state of a drug affects its solubility and dissolution behavior.

The melting point of a drug may vary for different salts, polymorphs, crystalline, and noncrystalline forms. In order to permit manufacture of tablets on commercial tablet presses, it is desirable that the drug melting point be greater than around 60° C., preferably greater than 100° C. to prevent drug melting during tablet manufacture. A preferred drug form in this instance is one that has the highest melting point. In addition, it is desirable to have a high melting point to assure chemical stability of a solid drug in a solid dosage form at high environmental storage temperatures which occur in direct sunlight and in geographic areas such as near the equator. If a soft-gel dosage form is desired, it is preferred to have a drug form which has a low melting point, to minimize crystallization of the drug in the dosage form. Thus, it can be seen that the desired melting point of a drug form depends on the intended use, and not all drug forms are equivalent.

When a drug's dose is high, or if a small dosage form is desired, the selection of a salt, hydrate, or solvate affects the potency per unit weight. For example, a drug salt with a higher molecular weight counterion will have a lower drug potency per gram than will a drug salt with a lower molecular weight counterion. It is desirable to choose a drug form which has the highest potency per unit weight.

The method of preparation of different crystalline polymorphs and noncrystalline forms varies widely from drug to drug. It is desirable that minimally toxic solvents be used in these methods, particularly for the last synthetic step, and particularly if the drug has a tendency to exist as a solvate with the solvent utilized in the last step of synthesis. Preferred drug forms are those which utilize less toxic solvents in their synthesis.

The ability of a drug to form good tablets at commercial scale depends upon a variety of drug physical properties, such as the Tableting Indices described in Hiestand H, Smith D. Indices of tableting performance. Powder Technology, 1984; 38:145-159. These indices may be used to identify forms of a drug, e.g. of atorvastatin calcium, which have superior tableting performance. One such index is the Brittle Fracture Index (BFI), which reflects brittleness, and ranges from 0 (good—low brittleness) to 1 (poor—high brittleness). Other useful indices or measures of mechanical properties, flow properties, and tableting performance include compression stress, absolute density, solid fraction, dynamic indentation hardness, ductility, elastic modulus, reduced elastic modulus, quasistatic indentation hardness, shear modulus, tensile strength, compromised tensile strength, best case bonding index, worst case bonding index, brittle/viscoelastic bonding index, strain index, viscoelastic number, effective angle of internal friction (from a shear cell test), cohesivity (from a powder avalanche test), and flow variability. A number of these measures are obtained on drug compacts, preferably prepared using a triaxial hydraulic press. Many of these measures are further described in Hancock B, Carlson G, Ladipo D, Langdon B, and Mullarney M. Comparison of the Mechanical Properties of the Crystalline and Amorphous Forms of a Drug Substance. International Journal of Pharmaceutics, 2002; 241:73-85.

Drug form properties which affect flow are important not just for tablet dosage form manufacture, but also for manufacture of capsules, suspensions, and sachets.

The particle size distribution of a drug powder can also have large effects on manufacturing processes, particularly through effects on powder flow. Different drug forms have different characteristic particle size distributions.

From the above discussion, it is apparent that there is no one drug form which is ideal for all therapeutic applications.

Thus it is important to seek a variety of unique drug forms, e.g. salts, polymorphs, noncrystalline forms, which may be used in various formulations. The selection of a drug form for a specific formulation or therapeutic application requires consideration of a variety of properties, as described above, and the best form for a particular application may be one which has one specific important good property while other properties may be acceptable or marginally acceptable.

We have now surprisingly and unexpectedly found novel forms of atorvastatin calcium. Thus the present invention provides new forms of atorvastatin calcium designated Forms XX, XXI, XXII, XXIII, XXIV, XXV, XXVI, XXVII, XXVIII, XXIX, XXX. The new forms of atorvastatin are purer, more stable, or have advantageous manufacturing and/or physical properties compared to forms of atorvastatin previously described.

In general, the new forms of atorvastatin calcium disclosed in the present application have high water solubility and high dissolution rates. This is an advantage for immediate release dosage forms since such forms need to be fully dissolved in the stomach before passing into the digestive tract. Additionally, some of the new forms can be prepared using solvents which are nontoxic. This avoids any residual solvents and their toxicity. Furthermore, some of the new forms have low hygroscopicity which, as explained above, is desirable from a packaging or handling aspect. Also, some of the new forms have advantageous tableting properties and can be conveniently made into a tablet. Additionally, some of the new forms can be easily and directly prepared, which provide a cost advantage. Also, some of the new forms are physically stable and not easily converted into other forms.

SUMMARY OF THE INVENTION

Accordingly, the present invention is directed to Form XX atorvastatin calcium characterized by the following x-ray powder diffraction (XRPD) pattern expressed in terms of degree 2θ and relative intensities with a relative intensity of >10% and relative peak width measured on a Shimadzu diffractometer with $CuK_a$ radiation:

| degree 2θ | Relative Intensity[a] | Relative Peak Width[b] |
|---|---|---|
| 7.5-9.0 | m | vb |
| 17.5-26.0 | s | vb |

[a]s = strong; m = medium
[b]vb = very broad (>1 degrees 2θ peak width)

In a second aspect, the present invention is directed to Form XXI atorvastatin calcium characterized by the following x-ray powder diffraction (XRPD) pattern expressed in terms of degree 2θ and relative intensities with a relative intensity of >10% and relative peak width measured on a Shimadzu diffractometer with $CuK_a$ radiation:

| degree 2θ | Relative Intensity[a] | Relative Peak Width[b] |
|---|---|---|
| 3.1 | w | b |
| 4.1 | w | b |
| 5.0 | w | b |
| 6.3 | w | b |
| 7.6 | s | b |
| 8.6 | m | b, sh |
| 9.2 | w | b, sh |
| 10.1 | w | b |
| 12.2 | w | b |
| 16.7 | m | vb |
| 18.2 | m | vb |
| 19.2 | m | vb |
| 20.1 | m | vb |
| 20.5 | w | vb |
| 23.1 | m | vb, sh |
| 29.6 | w | vb |

[a]s = strong; m = medium; w = weak
[b]b = broad, sh = shoulder, vb = very broad (>1 degrees 2θ peak width)

In a third aspect, the present invention is directed to Form XXII atorvastatin calcium characterized by the following x-ray powder diffraction (XRPD) pattern expressed in terms of degree 2θ and relative intensities with a relative intensity of >10% and relative peak width measured on a Shimadzu diffractometer with $CuK_a$ radiation:

| degree 2θ | Relative Intensity[a] | Relative Peak Width[b] |
|---|---|---|
| 4.0 | m | b |
| 4.9 | w | b |
| 8.0 | m | b |
| 10.0 | s | b |
| 11.1 | w | b |
| 11.7 | w | b |
| 12.2 | w | b |
| 13.1 | w | b, sh |
| 13.5 | m | b |
| 14.0 | w | b |
| 14.8 | w | b, sh |
| 16.1 | m | b |
| 16.4 | m | b, sh |
| 17.0 | m | b |
| 17.4 | m | b, sh |
| 17.7 | m | b, sh |
| 19.2 | w | b |
| 20.0 | m | b |
| 20.3 | m | b |
| 21.3 | w | b |
| 22.6 | w | b |
| 24.5 | w | vb |
| 27.0 | w | b |
| 28.1 | w | b |
| 28.9 | w | vb |
| 29.4 | w | vb |

[a]s = strong; m = medium; w = weak
[b]b = broad, sh = shoulder, vb = very broad (>1 degrees 2θ peak width)

In a fourth aspect, the present invention is directed to Form XXIII atorvastatin calcium characterized by the following x-ray powder diffraction (XRPD) pattern expressed in terms of degree 2θ and relative intensities with a relative intensity of >10% and relative peak width measured on a Shimadzu diffractometer with $CuK_a$ radiation:

| degree 2θ | Relative Intensity[a] | Relative Peak Width[b] |
|---|---|---|
| 3.2 | w | b |
| 4.1 | w | b |
| 5.0 | w | b |
| 6.3 | w | b |
| 7.2 | w | b, sh |
| 7.7 | s | b |
| 8.1 | m | b |
| 8.5 | m | b |
| 9.1 | w | b |
| 10.1 | w | b |
| 10.5 | w | b |
| 12.1 | w | b |
| 12.8 | w | b |
| 13.3 | w | b |

| degree 2θ | Relative Intensity[a] | Relative Peak Width[b] |
|---|---|---|
| 16.7 | m | vb |
| 18.4 | m | vb |
| 19.1 | m | b |
| 20.2 | m | vb |
| 21.0 | w | b |
| 21.4 | m | b |
| 23.2 | m | vb |
| 24.3 | w | b |
| 25.2 | w | b |
| 29.3 | w | b |

[a]s = strong; m = medium; w = weak
[b]b = broad, sh = shoulder, vb = very broad (>1 degrees 2θ peak width)

In a fifth aspect, the present invention is directed to Form XXIV atorvastatin calcium characterized by the following x-ray powder diffraction (XRPD) pattern expressed in terms of degree 2θ and relative intensities with a relative intensity of >10% and relative peak width measured on a Shimadzu diffractometer with CuK$_a$ radiation:

| degree 2θ | Relative Intensity[a] | Relative Peak Width[b] |
|---|---|---|
| 2.9 | m | b |
| 4.6 | w | b |
| 5.2 | w | b |
| 7.4 | m | b, sh |
| 7.8 | s | b |
| 8.7 | m | b |
| 9.5 | s | b |
| 10.0 | w | b |
| 12.2 | w | vb |
| 12.5 | w | b |
| 13.4 | w | b |
| 13.9 | w | b |
| 17.3 | w | vb |
| 18.0 | m | b |
| 18.6 | m | b |
| 19.0 | m | b |
| 20.6 | w | b |
| 21.2 | w | vb |
| 22.3 | w | vb |
| 22.7 | s | b |
| 23.2 | m | b, sh |
| 24.2 | w | b |
| 24.5 | w | vb |
| 25.0 | w | vb |
| 26.4 | w | vb |
| 28.8 | w | vb |
| 31.8 | w | b |

[a]s = strong; m = medium; w = weak
[b]b = broad, sh = shoulder, vb = very broad (>1 degrees 2θ peak width)

In a sixth aspect, the present invention is directed to Form XXV atorvastatin calcium characterized by the following x-ray powder diffraction (XRPD) pattern expressed in terms of degree 2θ and relative intensities with a relative intensity of >10% and relative peak width measured on a Shimadzu diffractometer with CuK$_a$ radiation:

| degree 2θ | Relative Intensity[a] | Relative Peak Width[b] |
|---|---|---|
| 3.1 | w | b |
| 5.2 | w | vb |
| 6.4 | w | sh, b |
| 7.4 | s | vb |
| 7.9 | w | sh, vb |
| 8.7 | m | vb |
| 10.4 | w | vb |
| 12.0 | w | vb |
| 12.7 | w | vb |
| 16.6 | m | vb |
| 18.1 | m | vb |
| 19.2 | m | vb |
| 20.0 | m | b |
| 20.7 | m | b |
| 22.8 | m | vb |
| 23.2 | m | vb |
| 24.4 | m | vb |
| 25.6 | w | vb |
| 26.5 | w | vb |
| 29.3 | w | vb |

[a]s = strong; m = medium; w = weak
[b]b = broad, sh = shoulder, vb = very broad (>1 degrees 2θ peak width)

In a seventh aspect, the present invention is directed to Form XXVI atorvastatin calcium characterized by the following x-ray powder diffraction (XRPD) pattern expressed in terms of degree 2θ and relative intensities with a relative intensity of >10% and relative peak width measured on a Shimadzu diffractometer with CuK$_a$ radiation:

| degree 2θ | Relative Intensity[a] | Relative Peak Width[b] |
|---|---|---|
| 3.7 | w | b |
| 7.3 | w | b, sh |
| 8.4 | s | b |
| 9.0 | s | b |
| 12.2 | w | b |
| 16.0 | w | vb |
| 17.1 | m | vb |
| 17.7 | m | vb |
| 18.7 | m | b |
| 20.1 | s | b |
| 20.7 | m | b, sh |
| 22.3 | m | vb |
| 23.0 | m | vb |
| 25.2 | m | vb |
| 28.7 | w | vb |

[a]s = strong; m = medium; w = weak
[b]b = broad, sh = shoulder, vb = very broad (>1 degrees 2θ peak width)

In an eighth aspect, the present invention is directed to Form XXVII atorvastatin calcium characterized by the following x-ray powder diffraction (XRPD) pattern expressed in terms of degree 2θ and relative intensities with a relative intensity of >10% and relative peak width measured on a Shimadzu diffractometer with CuK$_a$ radiation:

| degree 2θ | Relative Intensity[a] | Relative Peak Width[b] |
|---|---|---|
| 3.5 | w | b, sh |
| 3.9 | m | b |
| 4.6 | w | b |
| 7.1 | w | vb, sh |
| 7.5 | s | b |
| 7.9 | m | vb, sh |
| 9.6 | m | b |
| 9.9 | m | b |
| 10.6 | w | b |
| 11.8 | w | b |
| 13.0 | w | vb |
| 15.3 | w | b |
| 16.6 | w | vb |
| 17.2 | w | vb |
| 18.7 | s | b |
| 22.6 | w | vb |

-continued

| degree 2θ | Relative Intensity$^a$ | Relative Peak Width$^b$ |
|---|---|---|
| 23.8 | w | b |
| 25.1 | w | b |

$^a$s = strong; m = medium; w = weak
$^b$b = broad, sh = shoulder, vb = very broad (>1 degrees 2θ peak width)

In an ninth aspect, the present invention is directed to Form XXVIII atorvastatin calcium characterized by the following x-ray powder diffraction (XRPD) pattern expressed in terms of degree 2θ and relative intensities with a relative intensity of >10% and relative peak width measured on a Bruker diffractometer with CuK$_\alpha$ radiation:

| degree 2θ | Relative Intensity$^a$ | Relative Peak Width$^b$ |
|---|---|---|
| 7.6 | s | b |
| 9.5 | m | b |
| 12.2 | w | b |
| 16.5 | m | b |
| 17.0 | m | b |
| 18.0 | w | b |
| 19.2 | w | b |
| 19.5 | w | b, sh |
| 20.5 | m | b |
| 20.9 | w | b |
| 21.5 | w | b |
| 21.8 | w | b, sh |
| 22.3 | m | vb |
| 23.3 | w | b |
| 23.8 | w | b |

$^a$s = strong; m = medium; w = weak
$^b$b = broad, sh = shoulder, vb = very broad (>1 degrees 2θ peak width)

In a tenth aspect, the present invention is directed to Form XXIX atorvastatin calcium characterized by the following x-ray powder diffraction (XRPD) pattern expressed in terms of degree 2θ and relative intensities with a relative intensity of >10% and relative peak width measured on a Bruker diffractometer with CuK$_\alpha$ radiation:

| degree 2θ | Relative Intensity$^a$ | Relative Peak Width$^b$ |
|---|---|---|
| 8.0 | m | b |
| 10.2 | w | b |
| 11.5 | m | b |
| 14.5 | w | b |
| 15.3 | w | b |
| 16.2 | m | vb |
| 18.0 | m | b |
| 19.6 | m | b |
| 20.2 | m | b |
| 20.6 | w | b |
| 21.4 | w | b |
| 22.3 | m | b |
| 23.0 | m | b |
| 23.9 | w | b |
| 24.2 | m | b |
| 24.9 | s | b |
| 25.9 | w | vb |
| 26.9 | w | b |
| 28.6 | w | b |
| 29.1 | w | b |
| 30.4 | w | b |
| 30.9 | w | b |

$^a$s = strong; m = medium; w = weak
$^b$b = broad, sh = shoulder, vb = very broad (>1 degrees 2θ peak width)

In an eleventh aspect, the present invention is directed to Form XXX atorvastatin calcium characterized by the following x-ray powder diffraction (XRPD) pattern expressed in terms of degree 2θ and relative intensities with a relative intensity of >10% and relative peak width measured on a Shimadzu diffractometer with CuK$_a$ radiation:

| degree 2θ | Relative Intensity$^a$ | Relative Peak Width$^b$ |
|---|---|---|
| 3.1 | s | b |
| 9.0 | m | b |
| 9.7 | w | b |
| 10.5 | w | b |
| 12.0 | w | b |
| 16.5 | w | b |
| 17.0 | m | b |
| 19.0 | m | b |
| 19.3 | w | b, sh |
| 19.9 | w | b |
| 20.9 | m | b |
| 21.1 | w | b |
| 21.6 | s | b |
| 22.5 | m | vb |
| 24.3 | m | b |
| 26.7 | w | b |
| 27.0 | w | b |
| 27.6 | w | b |
| 29.6 | w | b |
| 31.8 | w | b |

$^a$s = strong; m = medium; w = weak
$^b$b = broad, sh = shoulder, vb = very broad (>1 degrees 2θ peak width)

As inhibitors of HMG-CoA reductase, the novel forms of atorvastatin calcium are useful as hypolipidemic and hypocholesterolemic agents as well as agents in the treatment of osteoporosis, benign prostatic hyperplasia (BPH), and Alzheimer's disease.

A still further embodiment of the present invention is a pharmaceutical composition for administering an effective amount of Form XX, Form XXI, Form XXII, Form XXIII, Form XXIV, Form XXV, Form XXVI, Form XXVII, Form XXVIII, Form XXIX, or Form XXX atorvastatin calcium in unit dosage form in the treatment methods mentioned above. Finally, the present invention is directed to methods for production of Form XX, Form XXI, Form XXII, Form XXIII, Form XXIV, Form XXV, Form XXVI, Form XXVII, Form XXVIII, Form XXIX, or Form XXX atorvastatin calcium.

BRIEF DESCRIPTION OF THE DRAWINGS

The invention is further described by the following non-limiting examples which refer to the accompanying Forms XX, XXI, XXII, XXIII, XXIV, XXV, XXVI, XXVII, XXVIII, XXIX, and XXX, short particulars of which are given below.

Figure 1:
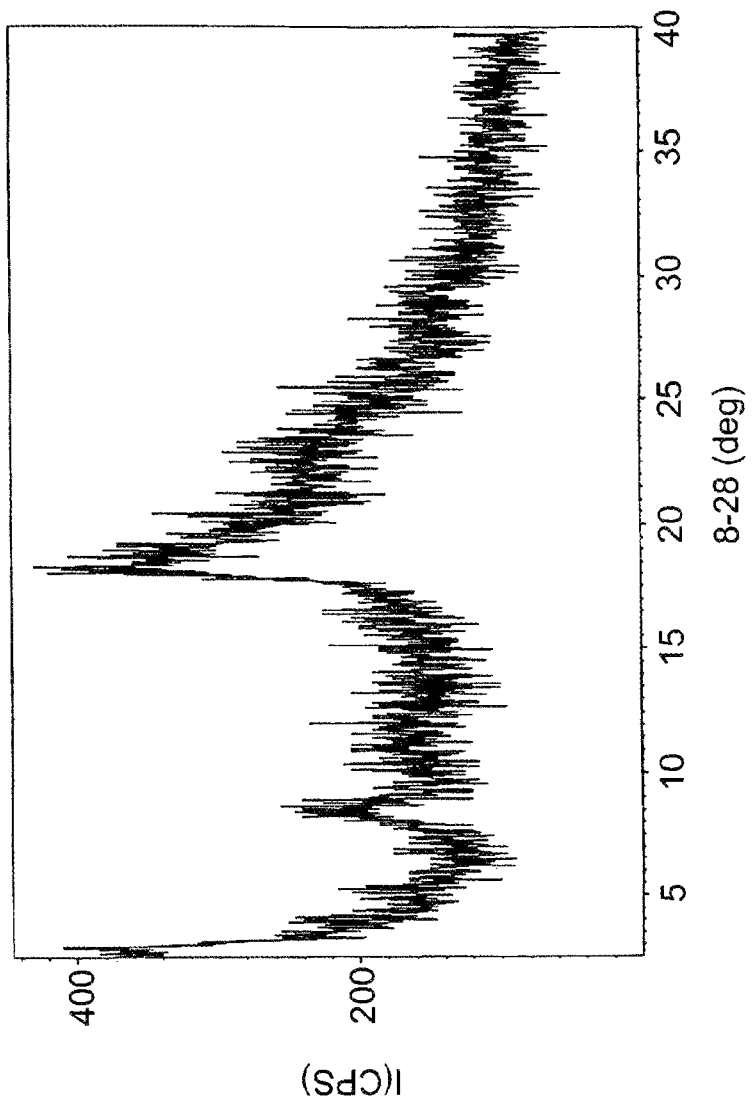
FIG. 1
Figure 2:
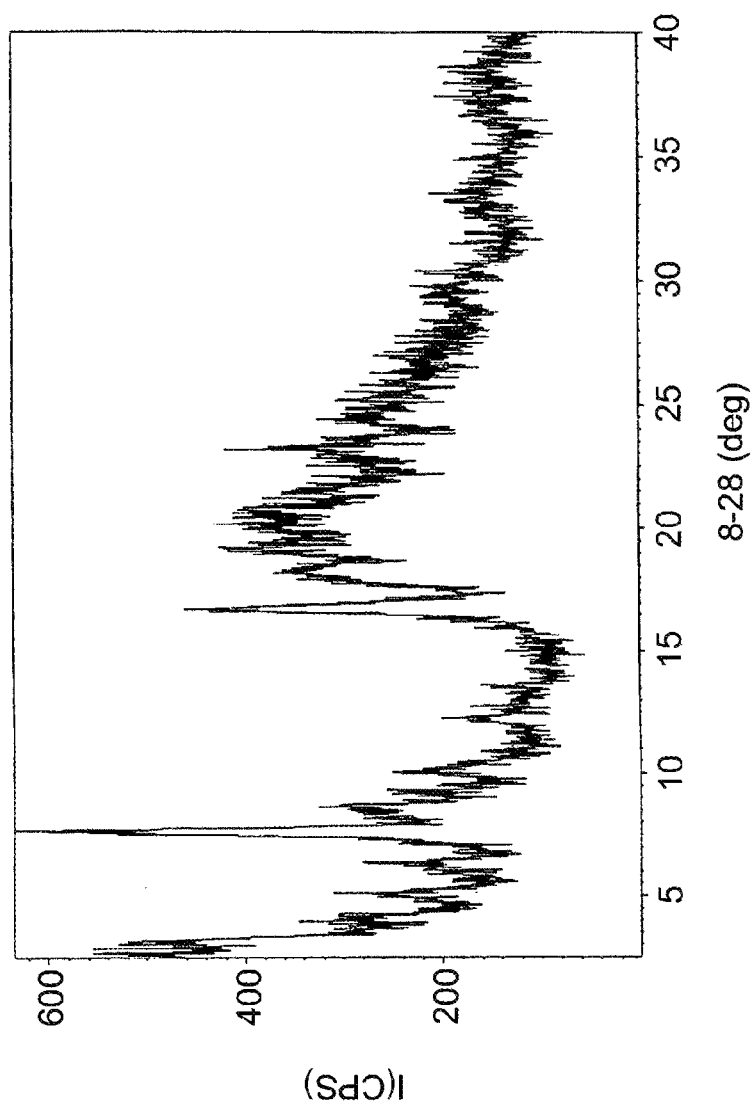
Figure 3:
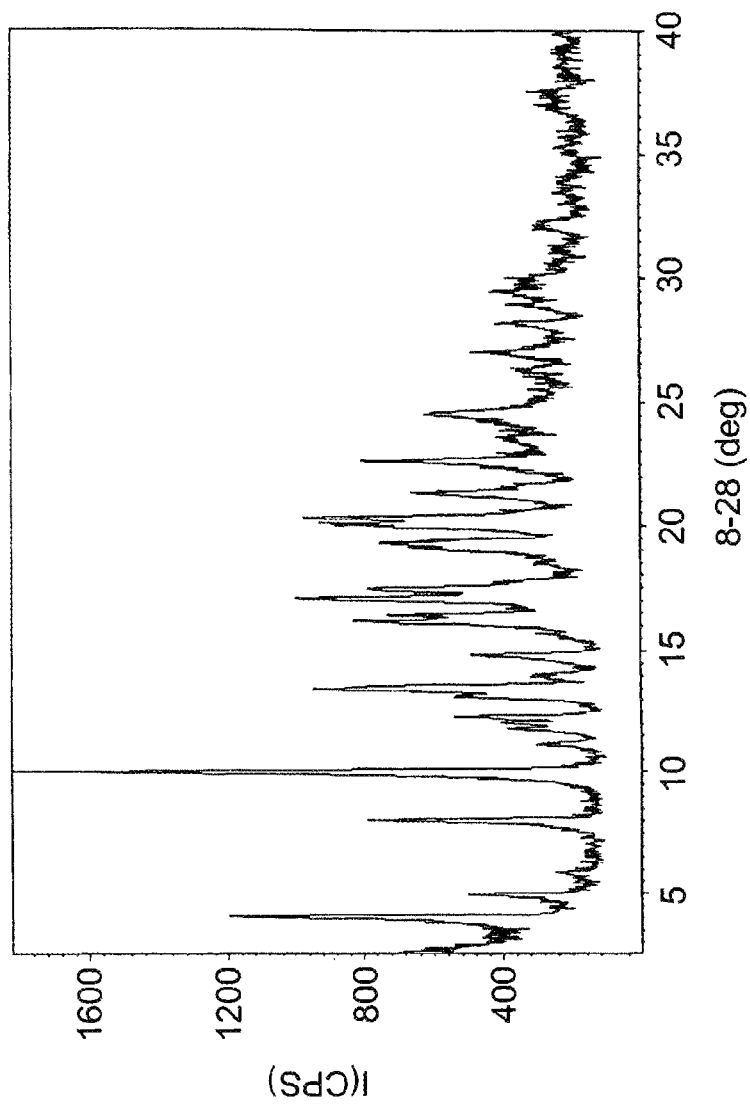
Figure 4:
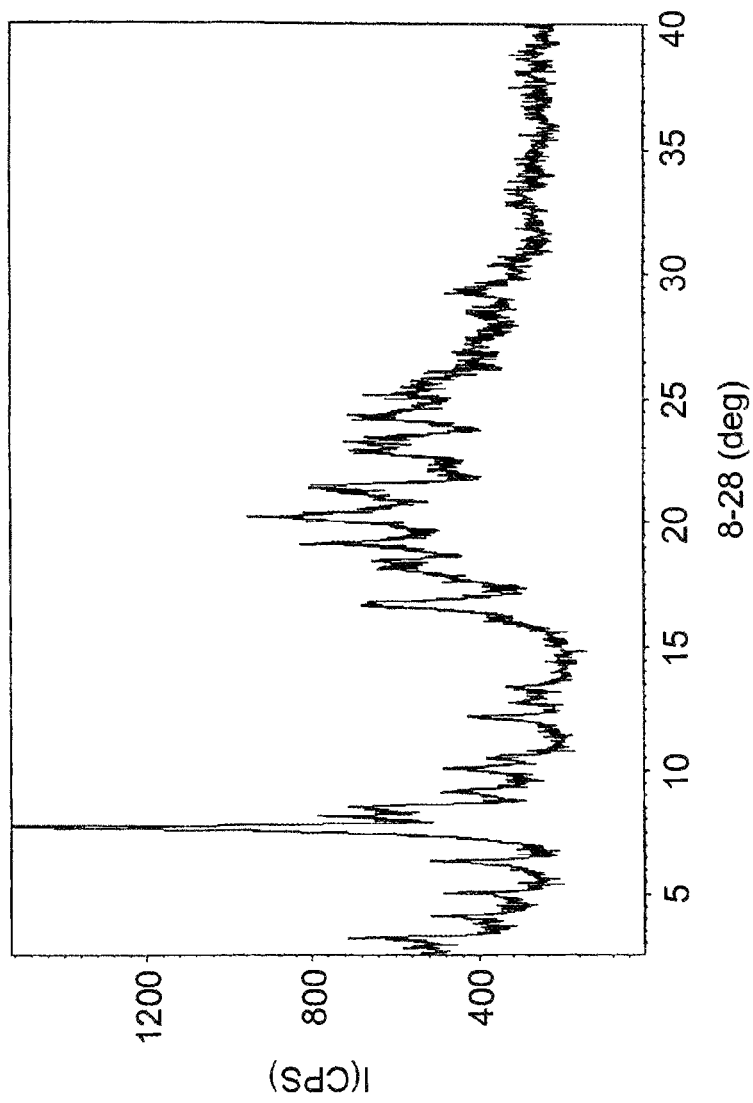
Figure 5:
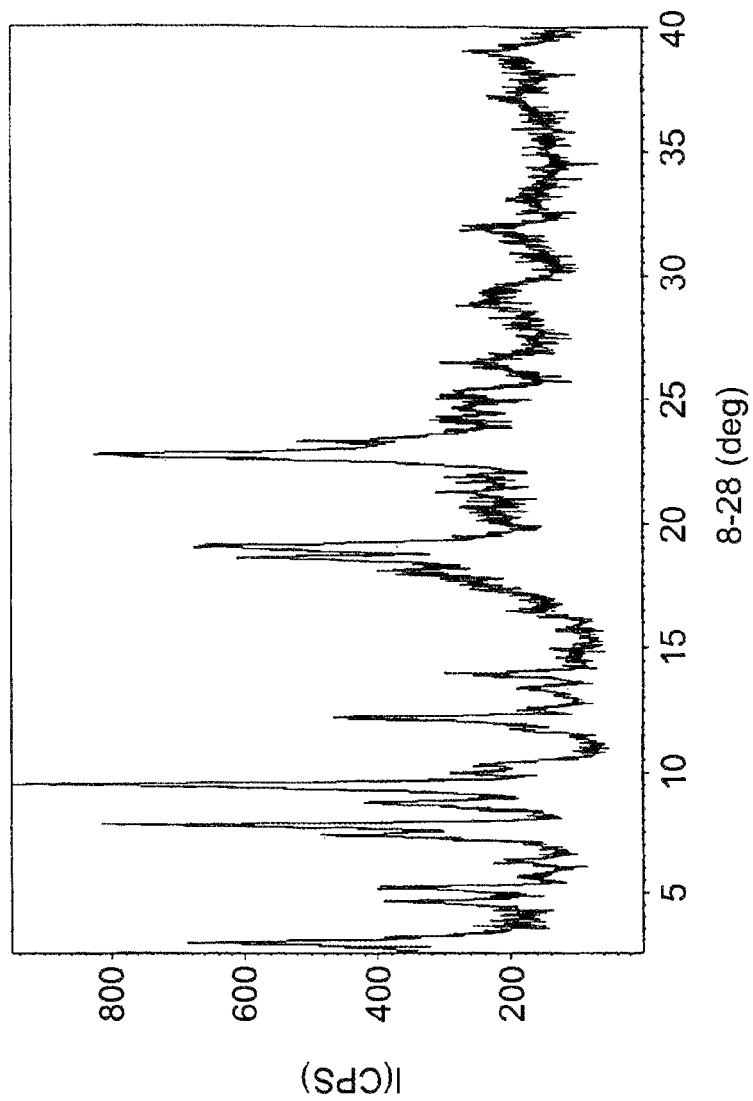
Figure 6:
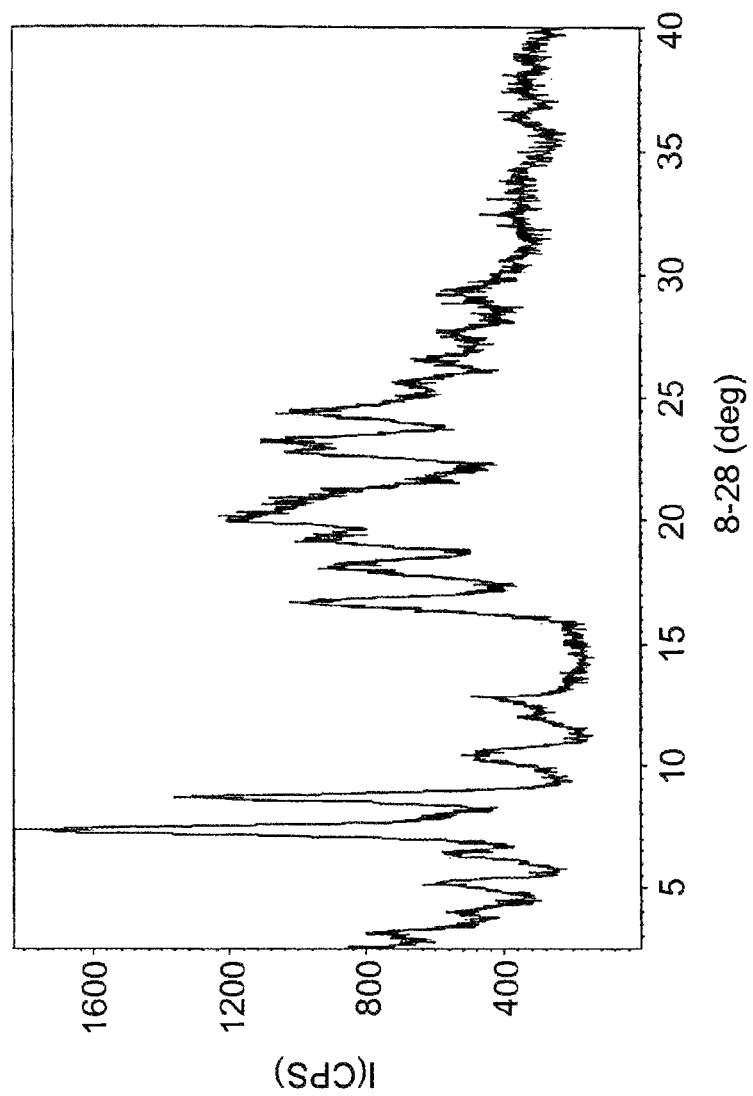
Figure 7:
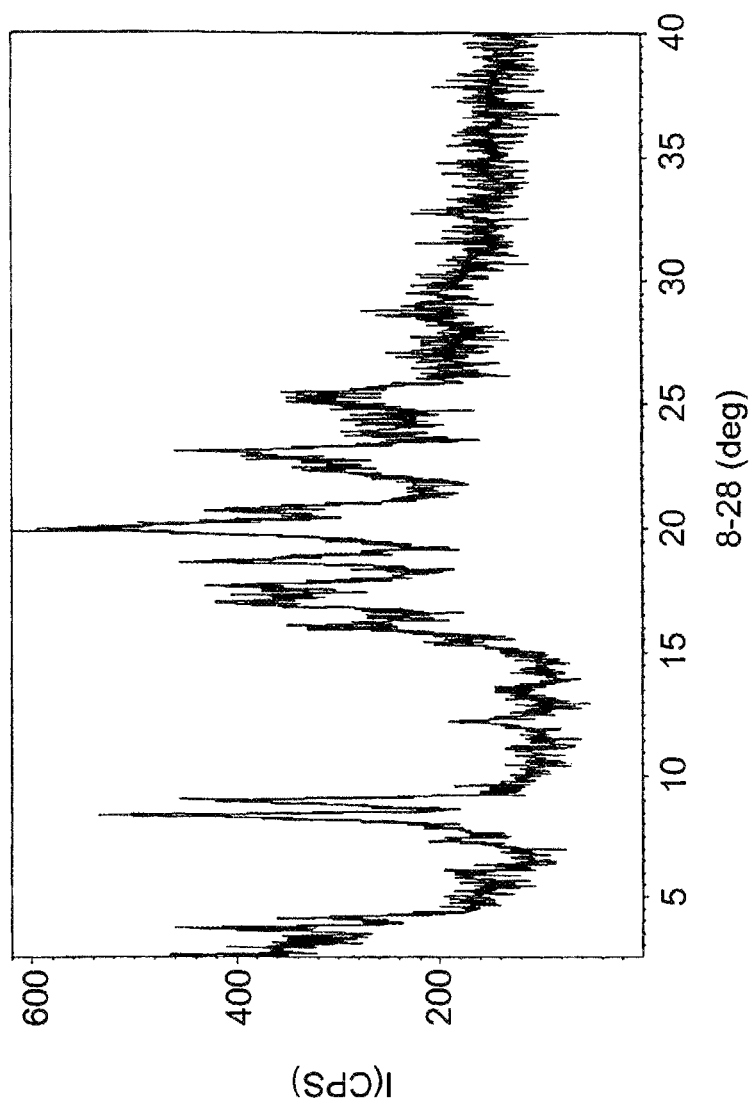
Figure 8:
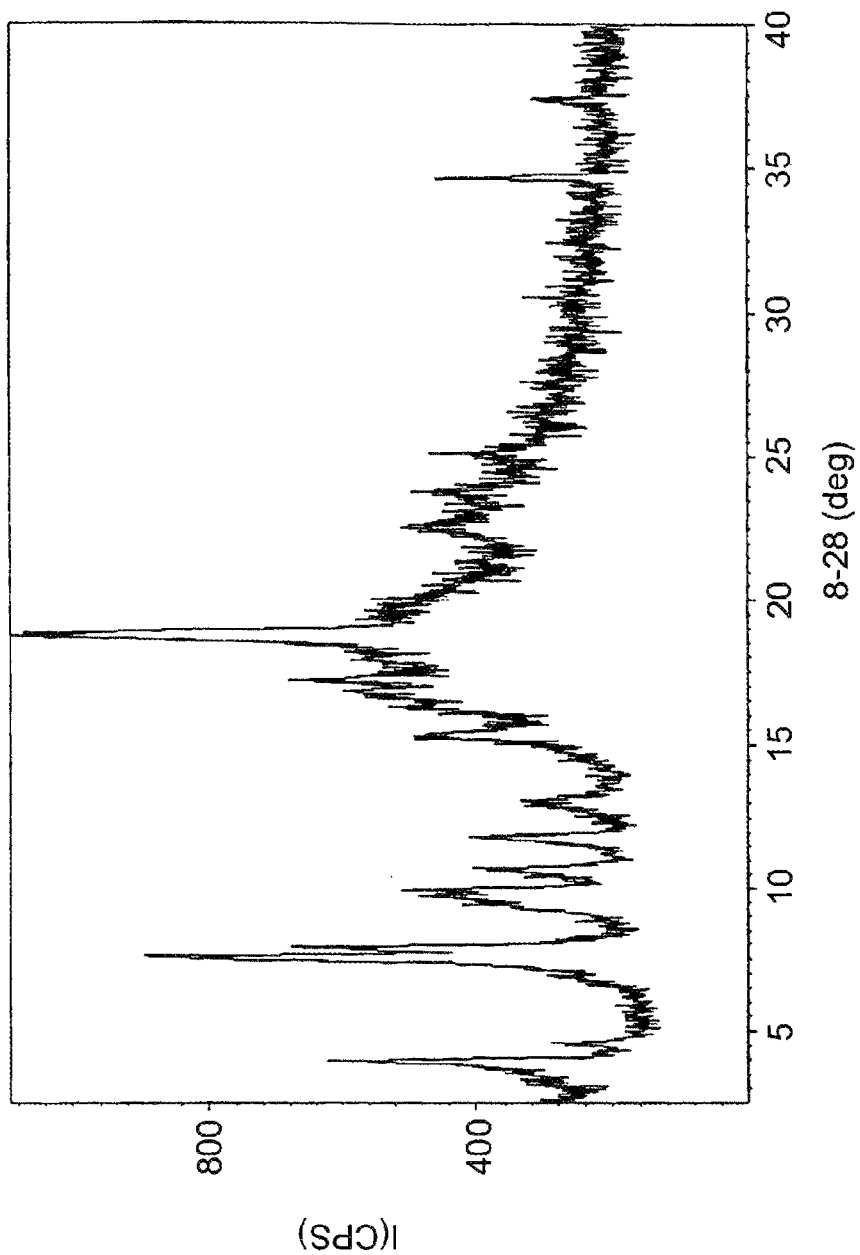
Figure 9:
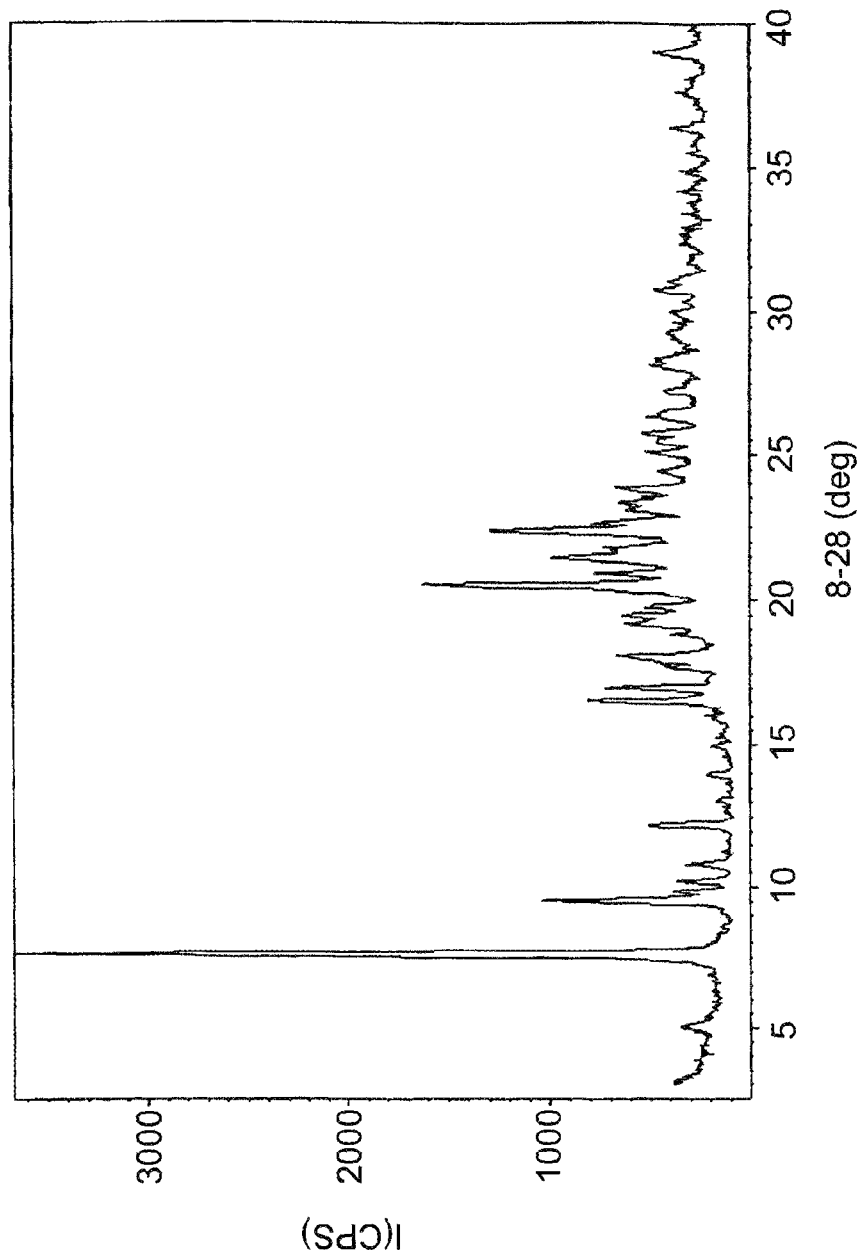
Figure 10:
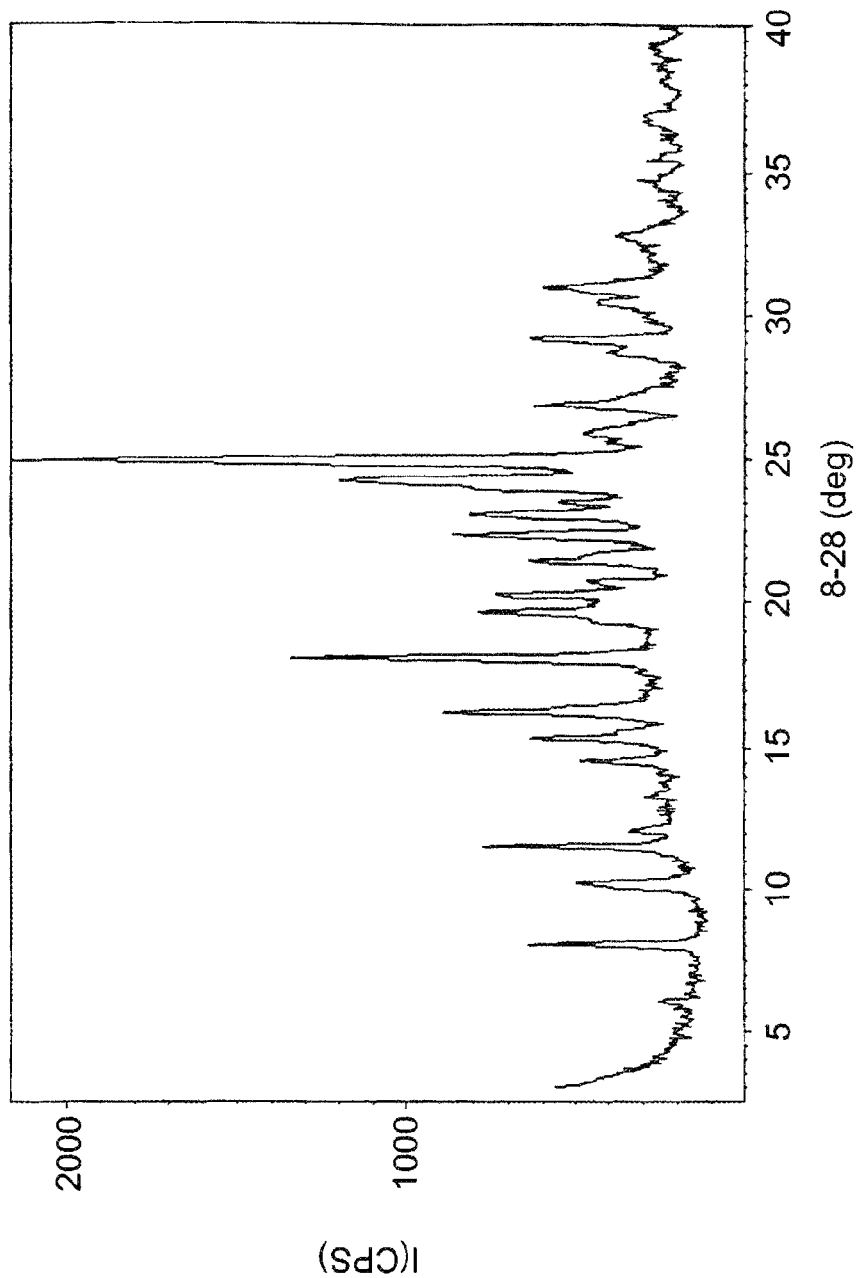
Figure 11:
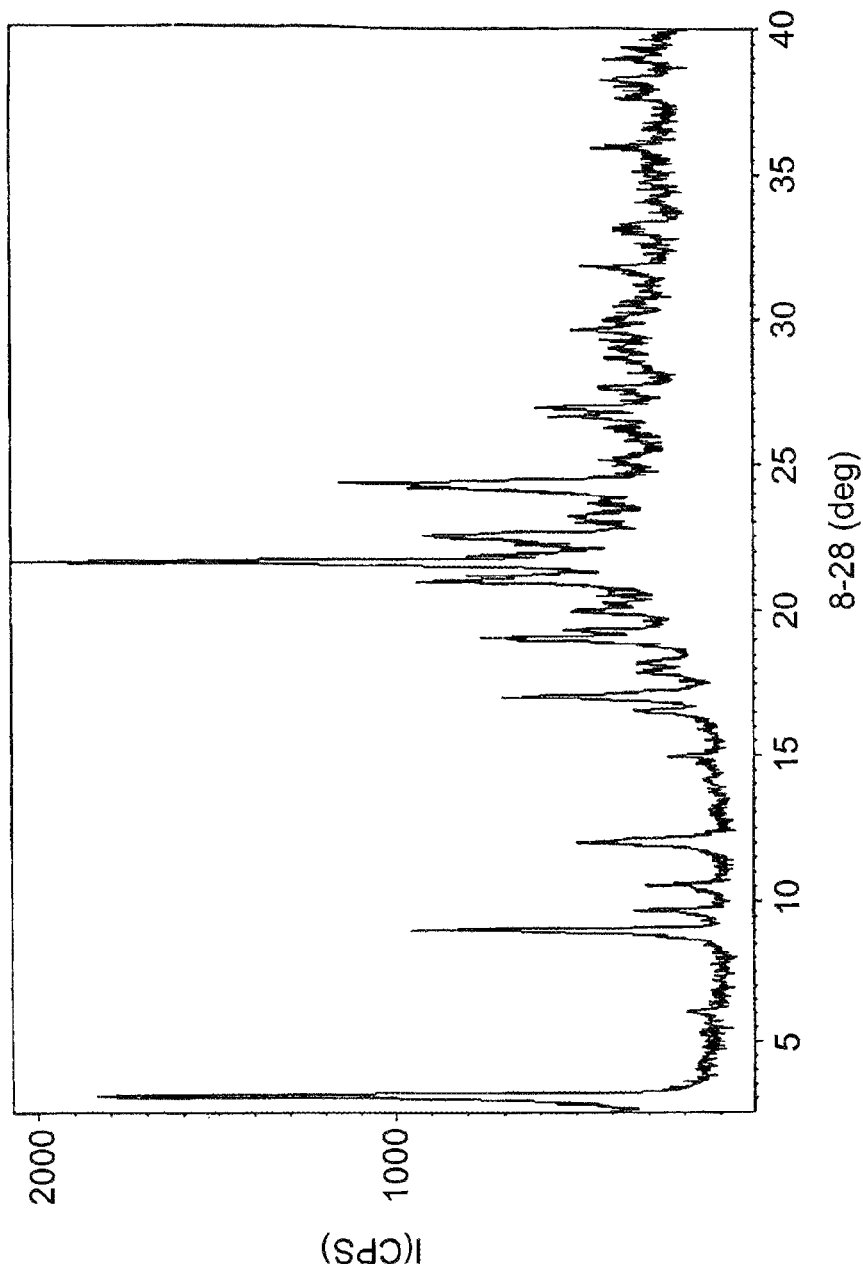
Figure 12:
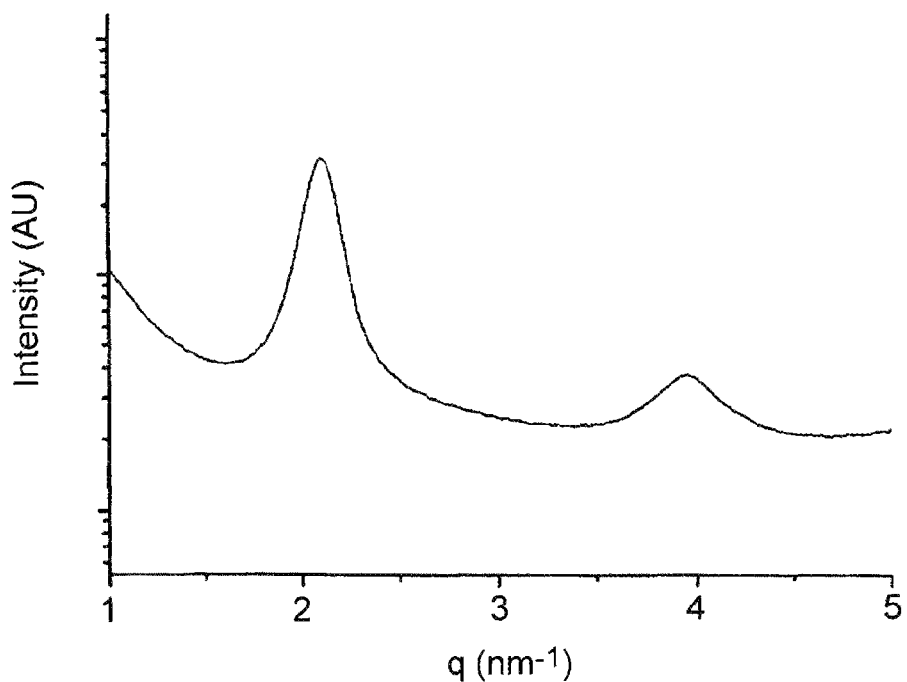
Figure 13:
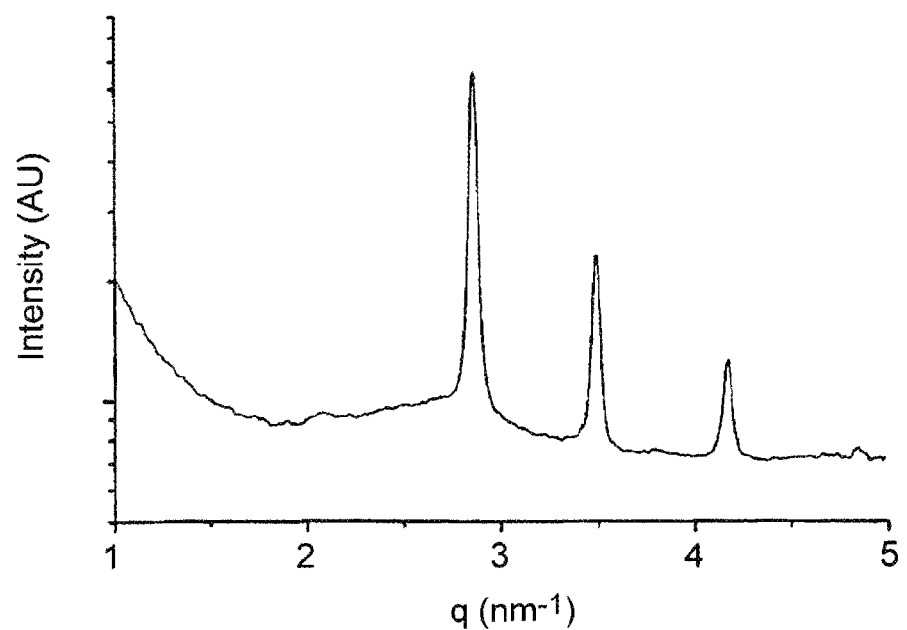
Figure 14:
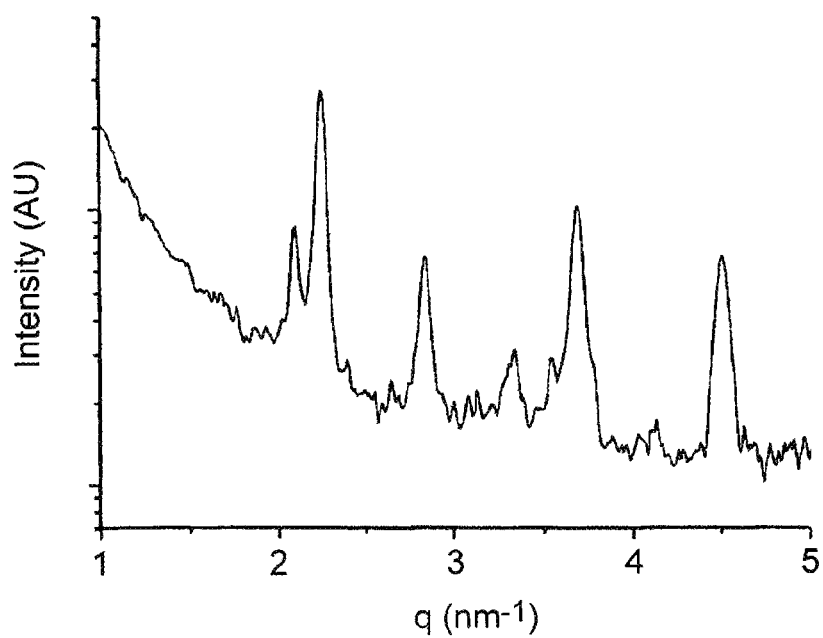
Figure 15:
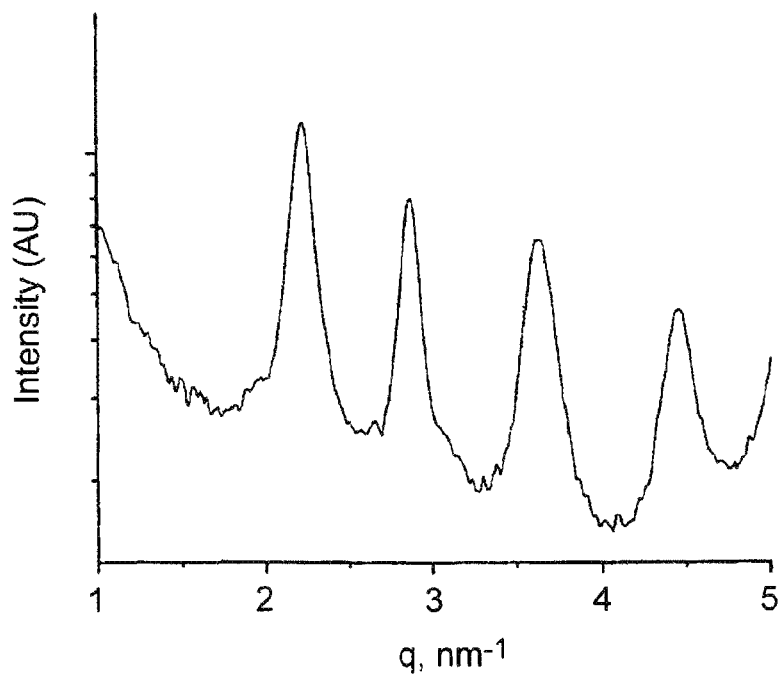
Figure 16:
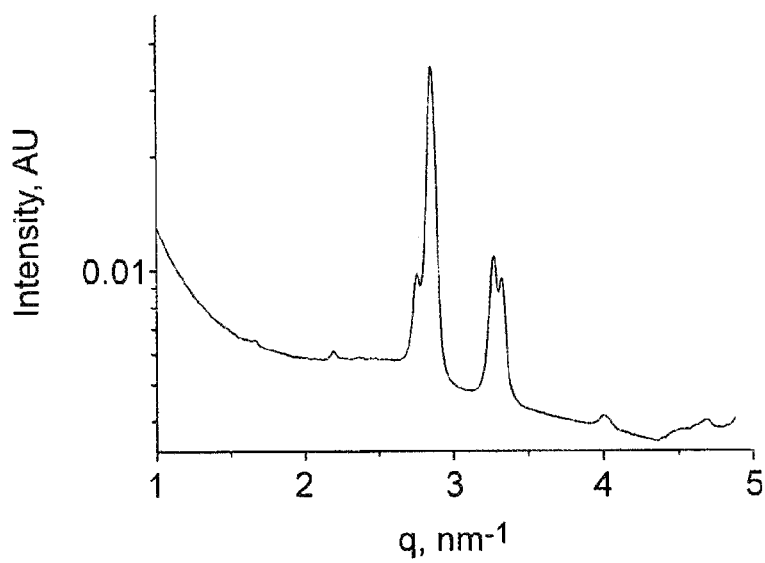
Figure 17:
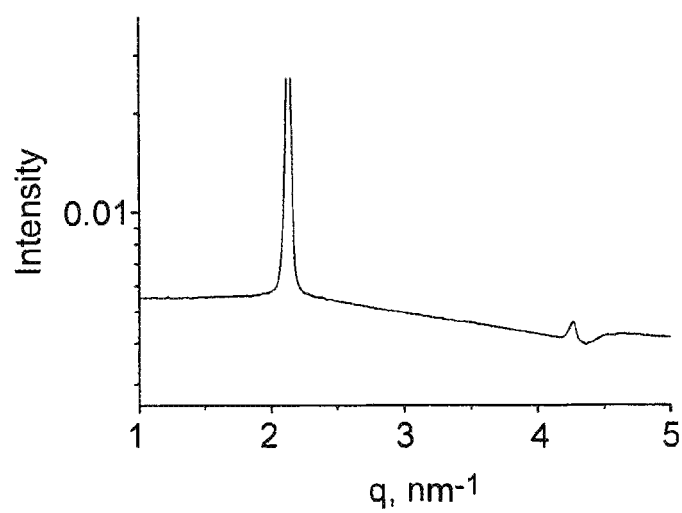
Figure 18:
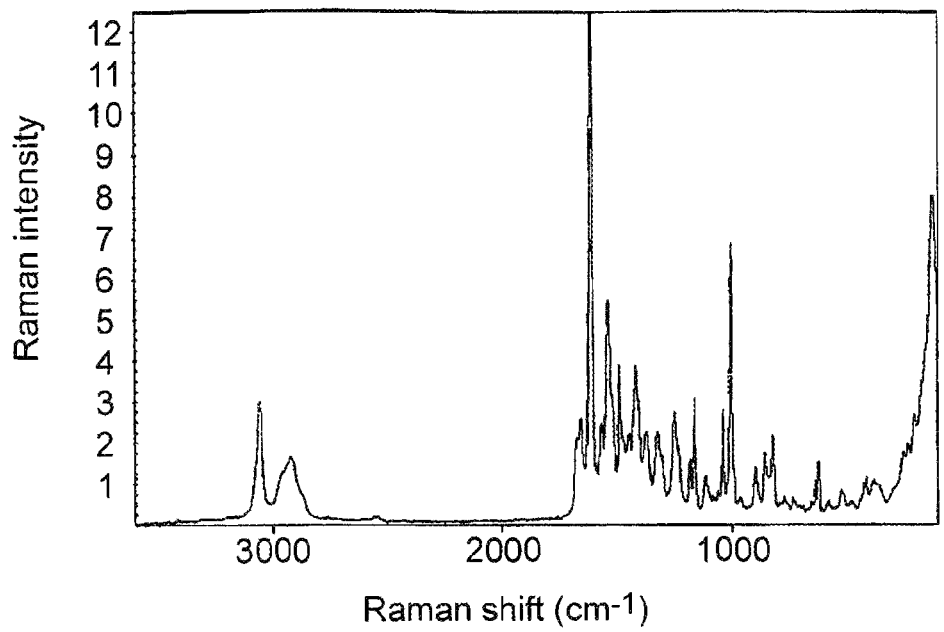
Figure 19:
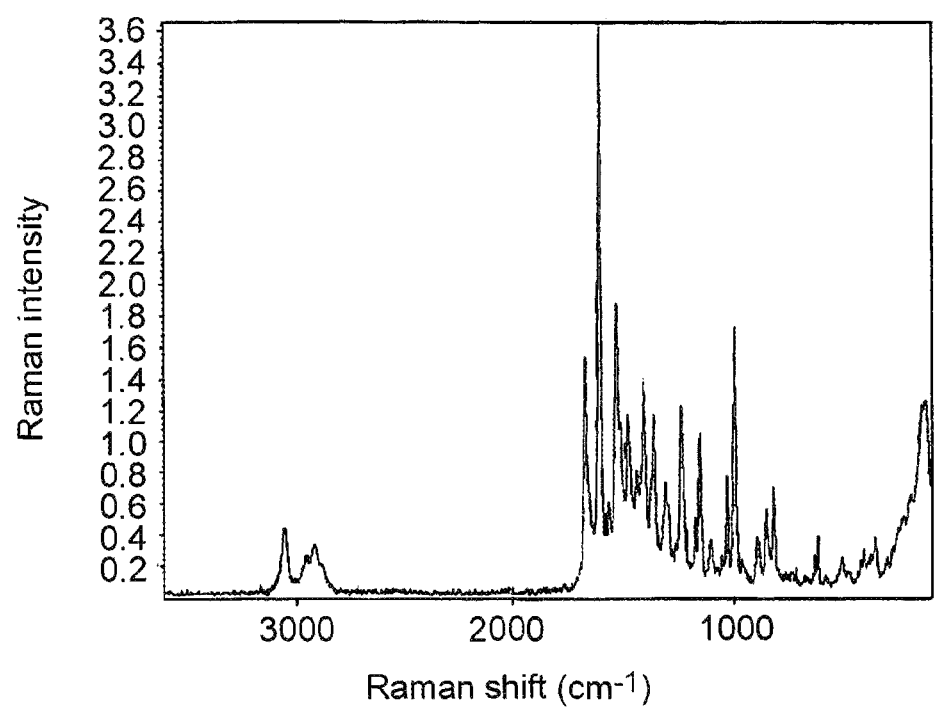
Figure 20:
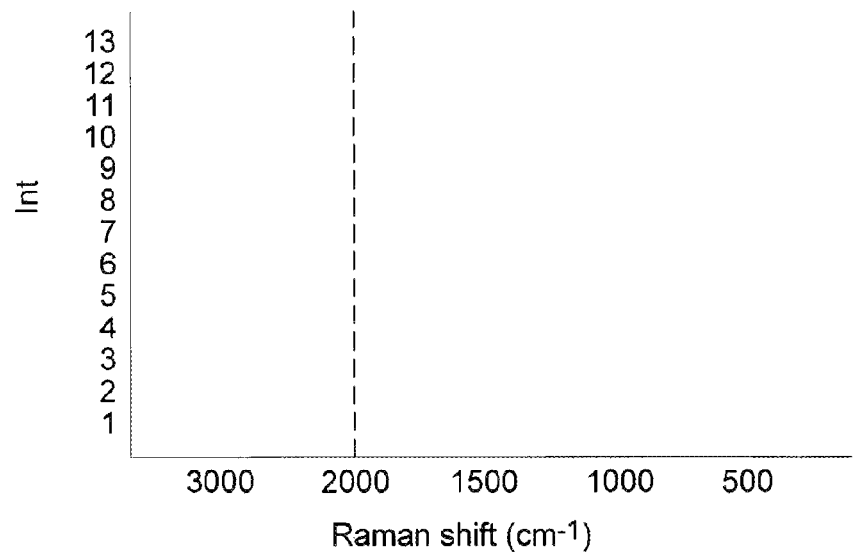
Figure 21:
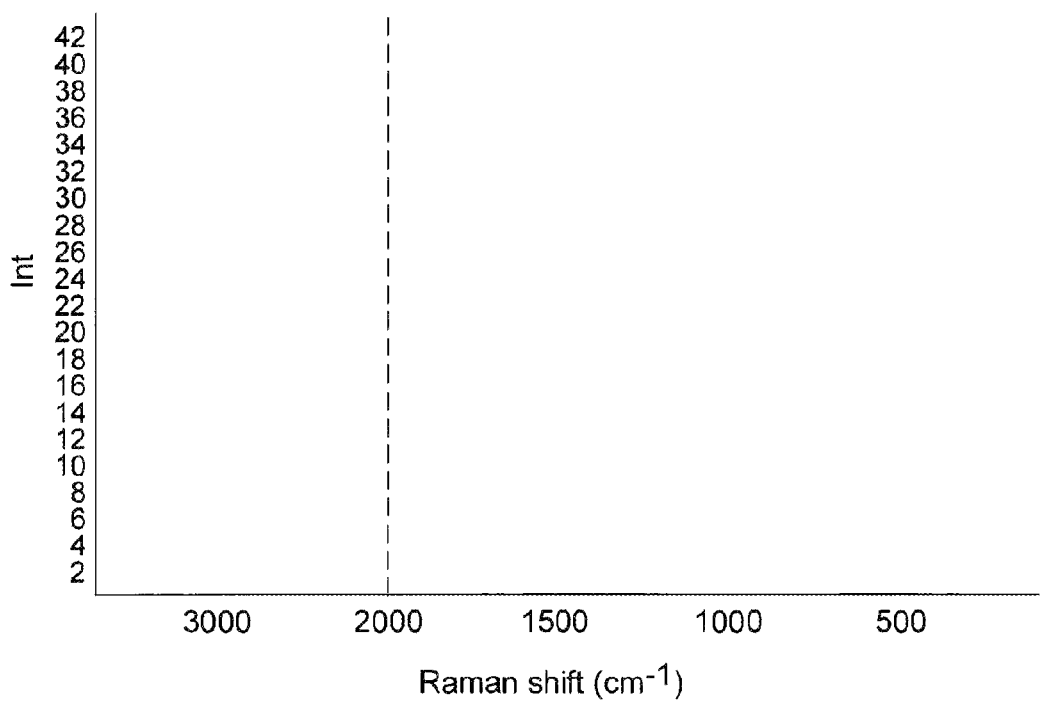
Figure 22:
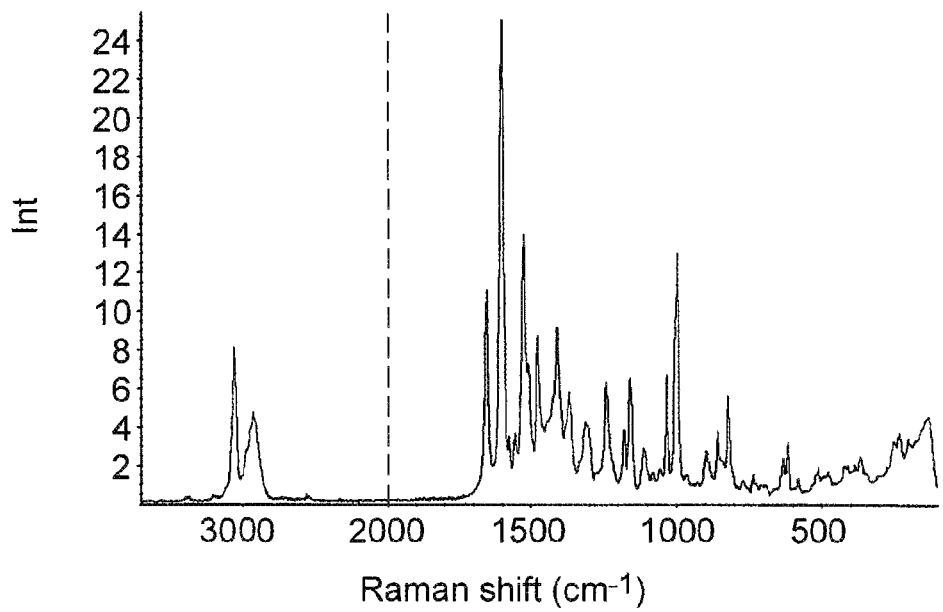
Figure 23:
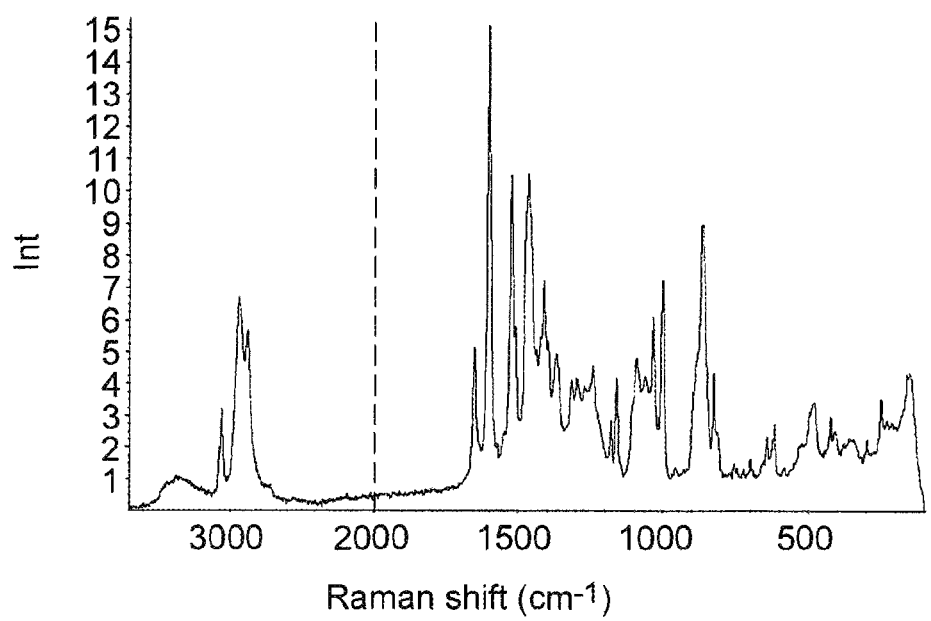
Figure 24:
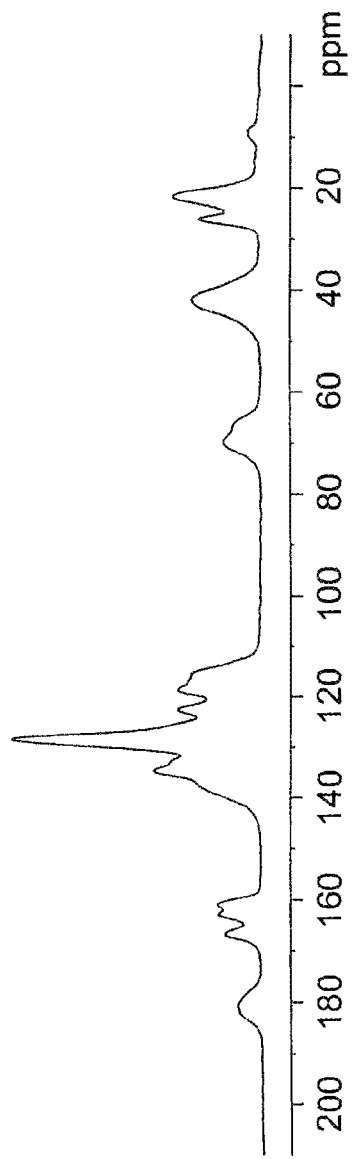
Figure 25:
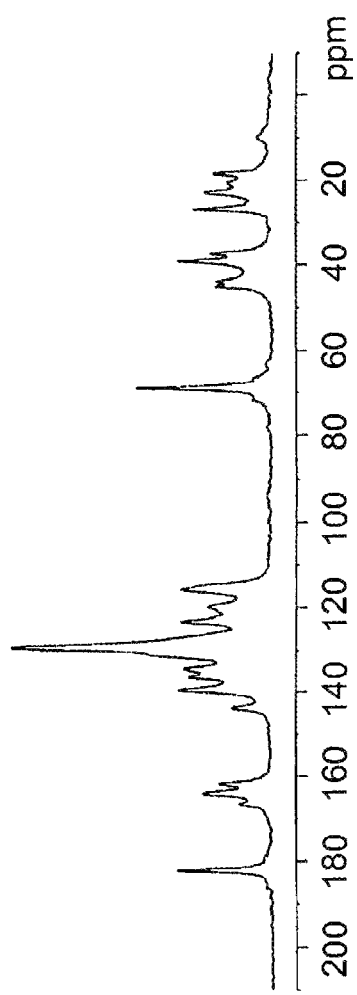
Figure 26:
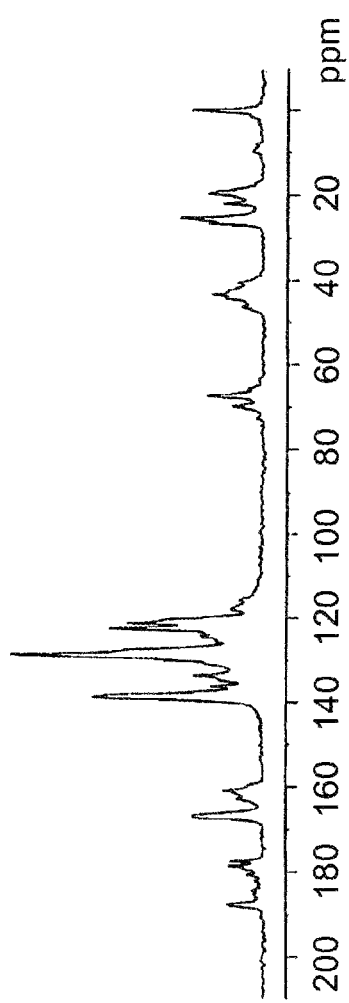
Figure 27:
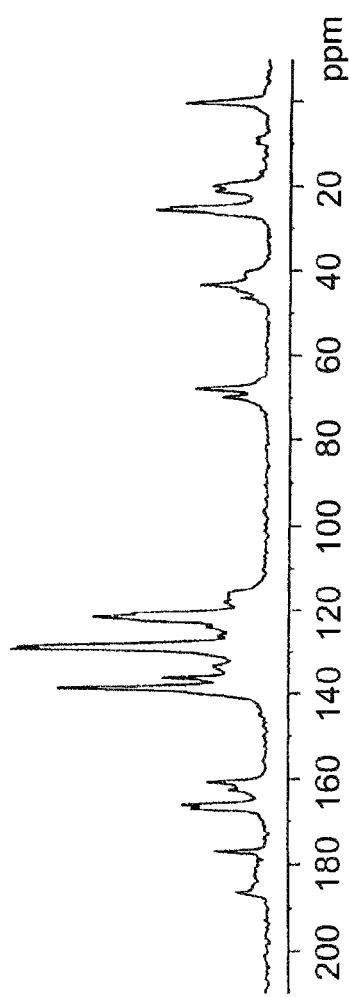
Figure 28:
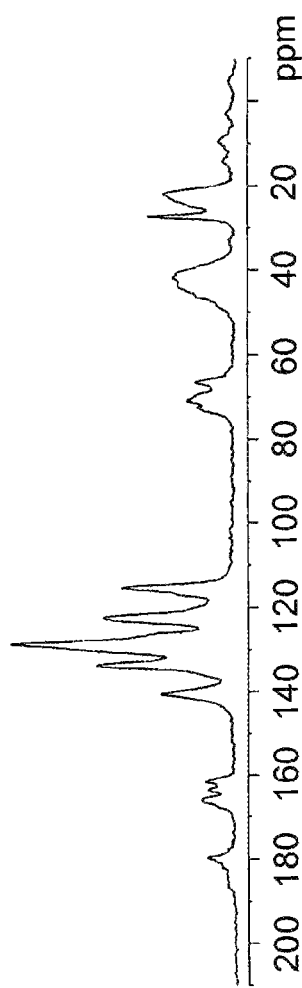
Figure 29:
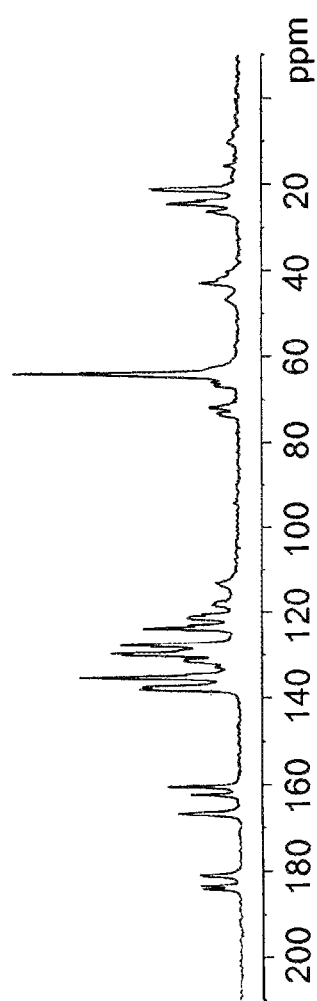
Figure 30:
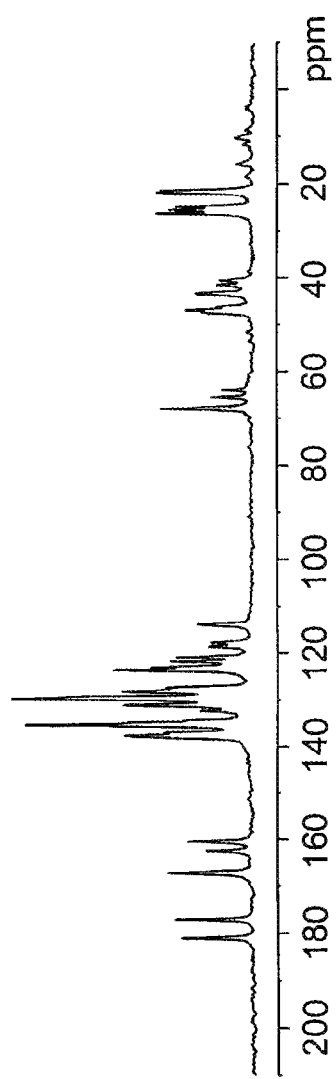
Figure 31:
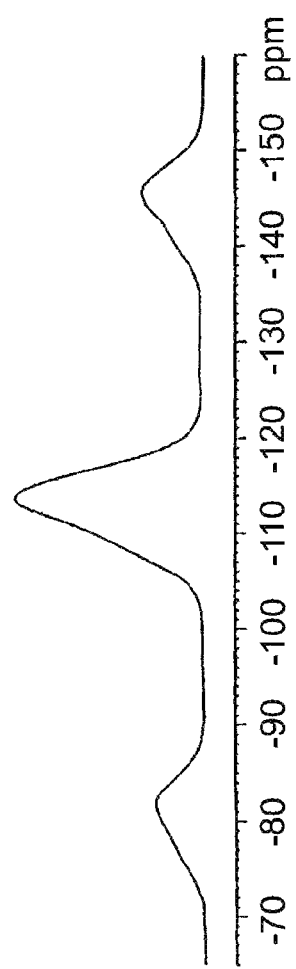
Figure 32:
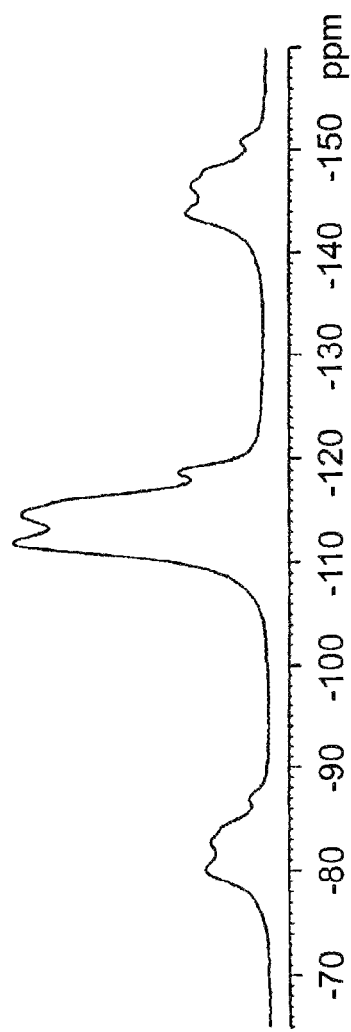
Figure 33:
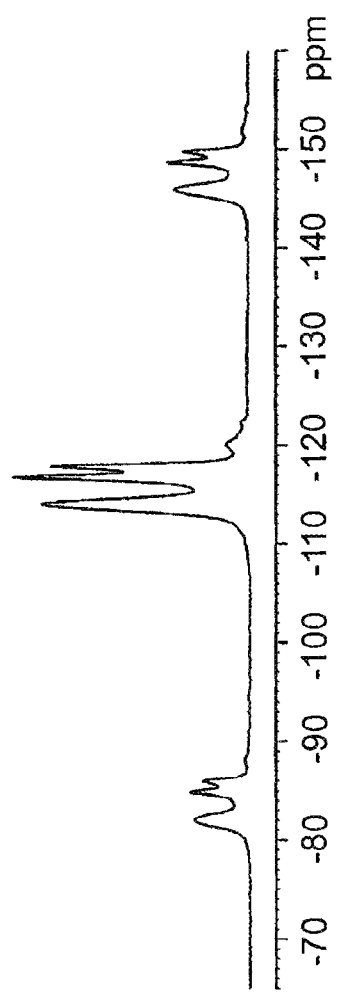
Figure 34:
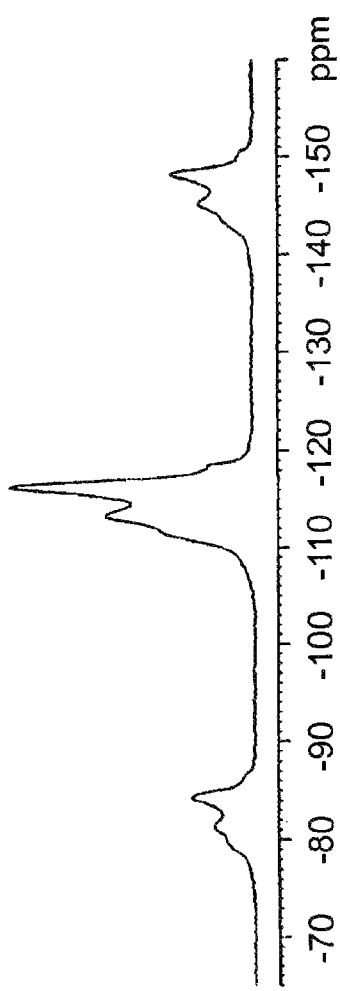
Figure 35:
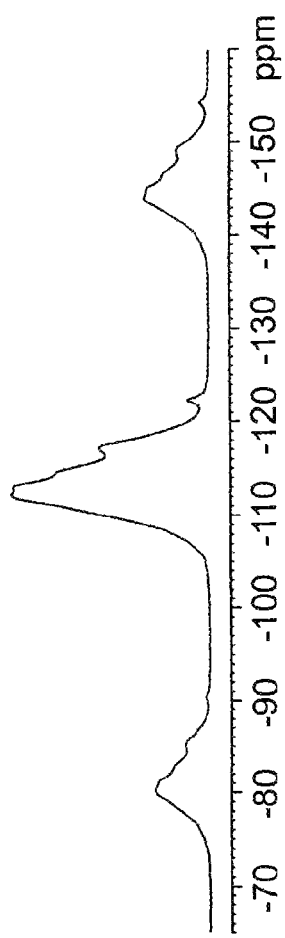

Diffractogram of Form XX atorvastatin calcium carried out on a Shimadzu XRD-6000 diffractometer.

FIG. 2

Diffractogram of Form XXI atorvastatin calcium carried out on a Shimadzu XRD-6000 diffractometer.

FIG. 3

Diffractogram of Form XXII atorvastatin calcium carried out on a Shimadzu XRD-6000 diffractometer.

FIG. 4

Diffractogram of Form XXIII atorvastatin calcium carried out on a Shimadzu XRD-6000 diffractometer.

FIG. 5

Diffractogram of Form XXIV atorvastatin calcium carried out on a Shimadzu XRD-6000 diffractometer.

FIG. 6

Diffractogram of Form XXV atorvastatin calcium carried out on a Shimadzu XRD-6000 diffractometer.

FIG. 7

Diffractogram of Form XXVI atorvastatin calcium carried out on a Shimadzu XRD-6000 diffractometer.

FIG. 8

Diffractogram of Form XXVII atorvastatin calcium carried out on a Shimadzu XRD-6000 diffractometer.

FIG. 9

Diffractogram of Form XXVIII atorvastatin calcium carried out on a Bruker diffractometer.

FIG. 10

Diffractogram of Form XXIX atorvastatin calcium carried out on a Bruker diffractometer.

FIG. 11

Diffractogram of Form XXX atorvastatin calcium carried out on a Shimadzu XRD-6000 diffractometer.

FIG. 12

Small angle diffractogram of Form XX atorvastatin calcium.

FIG. 13

Small angle diffractogram of Form XXII atorvastatin calcium.

FIG. 14

Small angle diffractogram of Form XXIV atorvastatin calcium.

FIG. 15

Small angle diffractogram of Form XXV atorvastatin calcium.

FIG. 16

Small angle diffractogram of Form XXVII atorvastatin calcium.

FIG. 17

Small angle diffractogram of Form XXX atorvastatin calcium.

FIG. 18

Raman spectrum of Form XX atorvastatin calcium.

FIG. 19

Raman spectrum of Form XXII atorvastatin calcium.

FIG. 20

Raman spectrum of Form XXIV atorvastatin calcium.

FIG. 21

Raman spectrum of Form XXV atorvastatin calcium.

FIG. 22

Raman spectrum of Form XXVII atorvastatin calcium.

FIG. 23

Raman spectrum of Form XXVIII atorvastatin calcium.

FIG. 24

Solid state $^{13}C$ nuclear magnetic resonance spectrum of Form XX atorvastatin calcium.

FIG. 25

Solid state $^{13}C$ nuclear magnetic resonance spectrum of Form XXII atorvastatin calcium.

FIG. 26

Solid state $^{13}C$ nuclear magnetic resonance spectrum of Form XXIV atorvastatin calcium.

FIG. 27

Solid state $^{13}C$ nuclear magnetic resonance spectrum of Form XXV atorvastatin calcium.

FIG. 28

Solid state $^{13}C$ nuclear magnetic resonance spectrum of Form XXVII atorvastatin calcium.

FIG. 29

Solid state $^{13}C$ nuclear magnetic resonance spectrum of Form XXVIII atorvastatin calcium.

FIG. 30

Solid state $^{13}C$ nuclear magnetic resonance spectrum of Form XXX atorvastatin calcium.

FIG. 31

Solid state $^{19}F$ nuclear magnetic resonance spectrum of Form XX atorvastatin calcium.

FIG. 32

Solid state $^{19}F$ nuclear magnetic resonance spectrum of Form XXII atorvastatin calcium.

FIG. 33

Solid state $^{19}F$ nuclear magnetic resonance spectrum of Form XXIV atorvastatin calcium.

FIG. 34

Solid state $^{19}F$ nuclear magnetic resonance spectrum of Form XXV atorvastatin calcium.

FIG. 35

Solid state $^{19}F$ nuclear magnetic resonance spectrum of Form XXVII atorvastatin calcium.

FIG. 38

Solid state $^{19}F$ nuclear magnetic resonance spectrum of Form XXVIII atorvastatin calcium.

FIG. 37

Solid state $^{19}F$ nuclear magnetic resonance spectrum of Form XXX atorvastatin calcium.

DETAILED DESCRIPTION OF THE INVENTION

Form XX, Form XXI, Form XXII, Form XXIII, Form XXIV, Form XXV, Form XXVI, Form XXVII, Form XXVIII, Form XXIX, or Form XXX atorvastatin calcium may be characterized by x-ray powder diffraction patterns, by their solid state nuclear magnetic resonance spectra (NMR), and/or their Raman spectra.

The "forms" of atorvastatin calcium disclosed in the present invention may exist as disordered crystals, liquid crystals, plastic crystals, mesophases, and the like. Forms that are related through disorder will have essentially the same major peak positions but the disordering process will cause broadening of these peaks. For many of the weaker peaks, the broadening may be so severe that they are no longer visible above the background. The peak broadening caused by disorder may in addition cause errors in the location of the exact peak position.

X-Ray Powder Diffraction

Form XX, Form XXI, Form XXII, Form XXIII, Form XXIV, Form XXV, Form XXVI, Form XXVII, Form XXVIII, Form XXIX, and Form XXX atorvastatin calcium were characterized by their X-ray powder diffraction pattern. Thus, the X-ray powder diffraction patterns of Forms XX, XXI, XXII, XXIII, XXIV, XXV, XXVI, XXVII, and XXX were carried out on a Shimadzu XRD-6000 X-ray diffractometer using Cu $K_\alpha$ radiation. This instrument is equipped with a fine focus X-ray tube. The tube voltage and amperage were set to 40 kV and 40 mA, respectively. The divergence and scattering slits were set at 1°, and the receiving slit was set at 0.15 mm. Diffraction radiation was detected by a NaI scintillation detector. A theta-two theta continuous scan at 3° C./min (0.4 sec/0.02° step) from 2.5 to 40°2θ was used. A silicon standard was analyzed each day to check the instrument alignment. Data were collected and analyzed using XRD-6000 V. 4.1. Samples were prepared for analysis by placing them in an aluminum holder.

The X-ray powder diffraction patterns of Forms XXVIII and XXIX were carried out on a Bruker D5000 diffractometer using Cu $K_\alpha$ radiation. The instrument was equipped with a fine focus X-ray tube. The tube voltage and amperage were set to 40 kV and 40 mA, respectively. The divergence and scattering slits were set at 1 mm, and the receiving slit was set at 0.6 mm. Diffracted radiation was detected by a Kevex PSI detector. A theta two theta continuous scan at 2.4°/min (1 sec/0.04° step) from 3.0 to 40°2θ was used. An alumina standard was analyzed to check the instrument alignment. Data were collected and analyzed using Bruker axs software Version 7.0. Samples were prepared for analysis by placing them in a quartz holder. It should be noted that Bruker Instruments purchased Siemans; thus, a Bruker D5000 instrument is essentially the same as a Siemans D5000.

To perform an X-ray diffraction measurement on a Bragg-Brentano instrument like the Shimadzu system or the Bruker system used for measurements reported herein, the sample is typically placed into a holder which has a cavity. The sample powder is pressed by a glass slide or equivalent to ensure a random surface and proper sample height. The sample holder is then placed into the Shimadzu instrument. The incident X-ray beam is directed at the sample, initially at a small angle relative to the plane of the holder, and then moved through an arc that continuously increases the angle between the incident beam and the plane of the holder. Measurement differences associated with such X-ray powder analyses result from a variety of factors including: (a) errors in sample preparation (e.g., sample height), (b) instrument errors (e.g. flat sample errors), (c) calibration errors, (d) operator errors (including those errors present when determining the peak locations), and (e) the nature of the material (e.g. preferred orientation and transparency errors). Calibration errors and sample height errors often result in a shift of all the peaks in the same direction. Small differences in sample height when using a flat holder will lead to large displacements in XRPD peak positions. A systematic study showed that, using a Shimadzu XRD-6000 in the typical Bragg-Brentano configuration, sample height difference of 1 mm lead to peak shifts as high as 1°2θ (Chen et al.; J Pharmaceutical and Biomedical Analysis, 2001; 26, 63). These shifts can be identified from the X-ray Diffractogram and can be eliminated by compensating for the shift (applying a systematic correction factor to all peak position values) or recalibrating the instrument. As mentioned above, it is possible to rectify measurements from the various machines by applying a systematic correction factor to bring the peak positions into agreement. In general, this correction factor will bring the measured peak positions from the Shimadzu or the Bruker into agreement with the expected peak positions and may be in the range of 0 to 0.2° 2θ.

Tables 1-11 list peak positions in degrees 2θ, relative intensities, and relative peak widths for X-ray powder diffraction patterns of each form of atorvastatin calcium disclosed in the present application. The relatively narrow peak positions were picked by the Shimadzu software using default settings. X-ray powder diffraction patterns were processed by the Shimadzu XRD-6000 version 2.6 software to automatically find peak positions. The "peak position" means the maximum intensity of a peaked intensity profile. To maximize accuracy and precision, the entire intensity profile is considered when selecting peak positions. Intensity spikes from large crystals and the expected intensity fluctuations from noise were considered in picking the position of a peak.

The following processes were used with the Shimadzu XRD6000 "Basic Process" version 2.6 algorithm:
1. Smoothing was done on all patterns.
2. The background was subtracted to find the net, relative intensity of the peaks.
3. A peak from $CuK_a$ alpha2 (1.5444 Å) wavelength was subtracted from the peak generated by $CuK_a$ alpha1 (1.5406 Å) peak at 50% intensity for all patterns.

Default values of the software were used in picking the peaks and all peak positions were rounded to $1/10^{th}$. Some of the XRPD patterns displayed very diffuse and very noisy patterns and the peak positions were determined manually, and expressed as a range of degree 2 theta (from the beginning of the broad peak to the end of the broad peak). All peak positions were rounded to 0.1°2θ. The following abbreviations are used to describe the peak intensity (s=strong; m=medium; w=weak) and the peak width (b=broad (where broad refers to peak widths of between 0.2 and 1.0 degrees 2θ, sh=shoulder, vb=very broad (where very broad refers to peaks with >1 degrees 2θ peak width)).

TABLE 1

XPRD Peak List for Form XX

| degree 2θ | Relative Intensity[a] | Relative Peak Width[b] |
|---|---|---|
| 7.5-9.0 | m | vb |
| 17.5-26.0 | s | vb |

[a] s = strong; m = medium; w = weak
[b] b = broad; sh = shoulder; vb = very broad (>1 degrees 2θ peak width)

TABLE 2

XPRD Peak List for Form XXI

| degree 2θ | Relative Intensity[a] | Relative Peak Width[b] |
|---|---|---|
| 3.1 | w | b |
| 4.1 | w | b |
| 5.0 | w | b |
| 6.3 | w | b |
| 7.6 | s | b |
| 8.6 | m | b, sh |
| 9.2 | w | b, sh |
| 10.1 | w | b |
| 12.2 | w | b |
| 16.7 | m | vb |
| 18.2 | m | vb |
| 19.2 | m | vb |
| 20.1 | m | vb |
| 20.5 | w | vb |
| 23.1 | m | vb, sh |
| 29.6 | w | vb |

[a] s = strong; m = medium; w = weak
[b] b = broad; sh = shoulder; vb = very broad (>1 degrees 2θ peak width)

TABLE 3

XPRD Peak List for Form XXII

| degree 2θ | Relative Intensity[a] | Relative Peak Width[b] |
|---|---|---|
| 4.0 | m | b |
| 4.9 | w | b |
| 8.0 | m | b |
| 10.0 | s | b |
| 11.1 | w | b |
| 11.7 | w | b |
| 12.2 | w | b |
| 13.1 | w | b, sh |
| 13.5 | m | b |
| 14.0 | w | b |
| 14.8 | w | b, sh |
| 16.1 | m | b |
| 16.4 | m | b, sh |
| 17.0 | m | b |
| 17.4 | m | b, sh |

TABLE 3-continued

XPRD Peak List for Form XXII

| degree 2θ | Relative Intensity[a] | Relative Peak Width[b] |
|---|---|---|
| 17.7 | m | b, sh |
| 19.2 | w | b |
| 20.0 | m | b |
| 20.3 | m | b |
| 21.3 | w | b |
| 22.6 | w | b |
| 24.5 | w | vb |
| 27.0 | w | b |
| 28.1 | w | b |
| 28.9 | w | vb |
| 29.4 | w | vb |

[a] s = strong; m = medium; w = weak
[b] b = broad; sh = shoulder; vb = very broad (>1 degrees 2θ peak width)

TABLE 4

XPRD Peak List for Form XXIII

| degree 2θ | Relative Intensity[a] | Relative Peak Width[b] |
|---|---|---|
| 3.2 | w | b |
| 4.1 | w | b |
| 5.0 | w | b |
| 6.3 | w | b |
| 7.2 | w | b, sh |
| 7.7 | s | b |
| 8.1 | m | b |
| 8.5 | m | b |
| 9.1 | w | b |
| 10.1 | w | b |
| 10.5 | w | b |
| 12.1 | w | b |
| 12.8 | w | b |
| 13.3 | w | b |
| 16.7 | m | vb |
| 18.4 | m | vb |
| 19.1 | m | b |
| 20.2 | m | vb |
| 21.0 | w | b |
| 21.4 | m | b |
| 23.2 | m | vb |
| 24.3 | w | b |
| 25.2 | w | b |
| 29.3 | w | b |

[a] s = strong; m = medium; w = weak
[b] b = broad; sh = shoulder; vb = very broad (>1 degrees 2θ peak width)

TABLE 5

XPRD Peak List for Form XXIV

| degree 2θ | Relative Intensity[a] | Relative Peak Width[b] |
|---|---|---|
| 2.9 | m | b |
| 4.6 | w | b |
| 5.2 | w | b |
| 7.4 | m | b, sh |
| 7.8 | s | b |
| 8.7 | m | b |
| 9.5 | s | b |
| 10.0 | w | b |
| 12.2 | w | vb |
| 12.5 | w | b |
| 13.4 | w | b |
| 13.9 | w | b |
| 17.3 | w | vb |
| 18.0 | m | b |
| 18.6 | m | b |
| 19.0 | m | vb |
| 20.6 | w | b |
| 21.2 | w | vb |

TABLE 5-continued

XPRD Peak List for Form XXIV

| degree 2θ | Relative Intensity[a] | Relative Peak Width[b] |
|---|---|---|
| 22.3 | w | vb |
| 22.7 | s | b |
| 23.2 | m | b, sh |
| 24.2 | w | b |
| 24.5 | w | vb |
| 25.0 | w | vb |
| 26.4 | w | vb |
| 28.8 | w | vb |
| 31.8 | w | b |

[a] s = strong; m = medium; w = weak
[b] b = broad; sh = shoulder; vb = very broad (>1 degrees 2θ peak width)

TABLE 6

XPRD Peak List for Form XXV

| degree 2θ | Relative Intensity[a] | Relative Peak Width[b] |
|---|---|---|
| 3.1 | w | b |
| 5.2 | w | vb |
| 6.4 | w | sh, b |
| 7.4 | s | vb |
| 7.9 | w | sh, vb |
| 8.7 | m | vb |
| 10.4 | w | vb |
| 12.0 | w | vb |
| 12.7 | w | vb |
| 16.6 | m | vb |
| 18.1 | m | vb |
| 19.2 | m | vb |
| 20.0 | m | b |
| 20.7 | m | b |
| 22.8 | m | vb |
| 23.2 | m | vb |
| 24.4 | m | vb |
| 25.6 | w | vb |
| 26.5 | w | vb |
| 29.3 | w | vb |

[a] s = strong; m = medium; w = weak
[b] b = broad; sh = shoulder; vb = very broad (>1 degrees 2θ peak width)

TABLE 7

XPRD Peak List for Form XXVI

| degree 2θ | Relative Intensity[a] | Relative Peak Width[b] |
|---|---|---|
| 3.7 | w | b |
| 7.3 | w | b, sh |
| 8.4 | s | b |
| 9.0 | s | b |
| 12.2 | w | b |
| 16.0 | w | vb |
| 17.1 | m | vb |
| 17.7 | m | vb |
| 18.7 | m | b |
| 20.1 | s | b |
| 20.7 | m | b, sh |
| 22.3 | m | vb |
| 23.0 | m | vb |
| 25.2 | m | vb |
| 28.7 | w | vb |

[a] s = strong; m = medium; w = weak
[b] b = broad; sh = shoulder; vb = very broad (>1 degrees 2θ peak width)

TABLE 8

XPRD Peak List for Form XXVII

| degree 2θ | Relative Intensity[a] | Relative Peak Width[b] |
|---|---|---|
| 3.5 | w | b, sh |
| 3.9 | m | b |
| 4.6 | w | b |
| 7.1 | w | vb, sh |
| 7.5 | s | b |
| 7.9 | m | vb, sh |
| 9.6 | m | b |
| 9.9 | m | b |
| 10.6 | w | b |
| 11.8 | w | b |
| 13.0 | w | vb |
| 15.3 | w | b |
| 16.6 | w | vb |
| 17.2 | w | b |
| 18.7 | s | b |
| 22.6 | w | vb |
| 23.8 | w | b |
| 25.1 | w | b |

[a]s = strong; m = medium; w = weak
[b]b = broad; sh = shoulder; vb = very broad (>1 degrees 2θ peak width)

TABLE 9

XPRD Peak List for Form XXVIII

| degree 2θ | Relative Intensity[a] | Relative Peak Width[b] |
|---|---|---|
| 7.6 | s | b |
| 9.5 | m | b |
| 12.2 | w | b |
| 16.5 | m | b |
| 17.0 | m | b |
| 18.0 | w | b |
| 19.2 | w | b |
| 19.5 | w | b, sh |
| 20.5 | m | b |
| 20.9 | w | b |
| 21.5 | w | b |
| 21.8 | w | b, sh |
| 22.3 | m | vb |
| 23.3 | w | b |
| 23.8 | w | b |

[a]s = strong; m = medium; w = weak
[b]b = broad; sh = shoulder; vb = very broad (>1 degrees 2θ peak width)

TABLE 10

XPRD Peak List for Form XXIX

| degree 2θ | Relative Intensity[a] | Relative Peak Width[b] |
|---|---|---|
| 8.0 | m | b |
| 10.2 | w | b |
| 11.5 | m | b |
| 14.5 | w | b |
| 15.3 | w | b |
| 16.2 | m | vb |
| 18.0 | m | b |
| 19.6 | m | b |
| 20.2 | m | b |
| 20.6 | w | b |
| 21.4 | w | b |
| 22.3 | m | b |
| 23.0 | m | b |
| 23.9 | w | b |
| 24.2 | m | b |
| 24.9 | s | b |
| 25.9 | w | vb |
| 26.9 | w | b |
| 28.6 | w | b |
| 29.1 | w | b |
| 30.4 | w | b |
| 30.9 | w | b |

[a]s = strong; m = medium; w = weak
[b]b = broad; sh = shoulder; vb = very broad (>1 degrees 2θ peak width)

TABLE 11

XPRD Peak List for Form XXX

| degree 2θ | Relative Intensity[a] | Relative Peak Width[b] |
|---|---|---|
| 3.1 | s | b |
| 9.0 | m | b |
| 9.7 | w | b |
| 10.5 | w | b |
| 12.0 | w | b |
| 16.5 | w | b |
| 17.0 | m | b |
| 19.0 | m | b |
| 19.3 | w | b, sh |
| 19.9 | w | b |
| 20.9 | m | b |
| 21.1 | w | b |
| 21.6 | s | b |
| 22.5 | m | vb |
| 24.3 | m | b |
| 26.7 | w | b |
| 27.0 | w | b |
| 27.6 | w | b |
| 29.6 | w | b |
| 31.8 | w | b |

[a]s = strong; m = medium; w = weak
[b]b = broad; sh = shoulder; vb = very broad (>1 degrees 2θ peak width)

Table 12 lists combinations of 2θ peaks for Forms XXI, XXII, XXIII, XXIV, XXV, XXVI, XXVII, XXVIII, XXIX, and XXX atorvastatin calcium, i.e., a set of x-ray diffraction lines that are unique to each form.

TABLE 12

Forms XXI, XXII, XXIII, XXIV, XXV, XXVI, XXVII, XXVIII, XXIX, and XXX.

| Form | degree 2θ |
|---|---|
| XXI | 3.1 |
|  | 4.1 |
|  | 5.0 |
|  | 7.6 |
|  | 16.7 |
|  | 18.2 |
|  | 19.2 |
|  | 20.1 |
|  | 20.5 |
|  | 23.1 |
| XXII | 4.0 |
|  | 8.0 |
|  | 10.0 |
|  | 13.5 |
|  | 16.1 |
|  | 16.4 |
|  | 17.0 |
|  | 17.4 |
|  | 19.2 |
|  | 20.0 |
|  | 20.3 |
| XXIII | 4.1 |
|  | 5.0 |
|  | 6.3 |

TABLE 12-continued

Forms XXI, XXII, XXIII, XXIV, XXV, XXVI, XXVII, XXVIII, XXIX, and XXX.

| Form | degree 2θ |
|---|---|
|  | 7.7 |
|  | 8.5 |
|  | 9.1 |
|  | 10.5 |
|  | 16.7 |
|  | 18.4 |
|  | 20.2 |
|  | 21.4 |
| XXIV | 2.9 |
|  | 7.4 |
|  | 7.8 |
|  | 8.7 |
|  | 9.5 |
|  | 10.0 |
|  | 12.2 |
|  | 18.0 |
|  | 18.6 |
|  | 19.0 |
|  | 22.7 |
| XXV | 3.1 |
|  | 5.2 |
|  | 7.4 |
|  | 8.7 |
|  | 10.4 |
|  | 12.7 |
|  | 16.6 |
|  | 18.1 |
|  | 19.2 |
|  | 20.0 |
|  | 20.7 |
|  | 23.2 |
|  | 24.4 |
| XXVI | 3.7 |
|  | 8.4 |
|  | 9.0 |
|  | 17.1 |
|  | 17.7 |
|  | 18.7 |
|  | 20.1 |
|  | 22.3 |
|  | 23.0 |
| XXVII | 3.9 |
|  | 4.5 |
|  | 7.1 |
|  | 7.5 |
|  | 9.6 |
|  | 10.6 |
|  | 11.8 |
|  | 13.0 |
|  | 15.3 |
|  | 18.7 |
| XXVIII | 7.6 |
|  | 9.5 |
|  | 12.2 |
|  | 16.5 |
|  | 17.0 |
|  | 18.0 |
|  | 20.5 |
|  | 21.5 |
|  | 22.3 |
| XXIX | 8.0 |
|  | 10.2 |
|  | 11.5 |
|  | 14.5 |
|  | 15.3 |
|  | 18.0 |
|  | 19.6 |
|  | 20.2 |
|  | 22.3 |
|  | 24.9 |
| XXX | 3.1 |
|  | 9.0 |
|  | 9.7 |
|  | 12.0 |
|  | 16.5 |
|  | 17.0 |
|  | 20.9 |
|  | 21.6 |
|  | 22.5 |
|  | 24.3 |

Further, Table 13 lists additional combinations of 2θ peaks for Forms XXI, XXII, XXIII, XXIV, XXV, XXVI, XXVII, XXVIII, XXIX, and XXX atorvastatin calcium, i.e., an additional set of x-ray diffraction lines that are unique to each form.

TABLE 13

Forms XX, XXI, XXII, XXIII, XXIV, XXV, XXVI, XXVII, XXVIII, XXIX, and XXX

| Form | Degree 2θ |
|---|---|
| Form XXI | 3.1 |
|  | 4.1 |
|  | 5.0 |
|  | 7.6 |
|  | 16.7 |
|  | 18.2 |
|  | 19.2 |
|  | 23.1 |
| Form XXII | 4.0 |
|  | 10.0 |
|  | 13.5 |
|  | 17.0 |
|  | 19.2 |
|  | 20.3 |
| Form XXIII | 4.1 |
|  | 5.0 |
|  | 6.3 |
|  | 7.7 |
|  | 8.5 |
|  | 9.1 |
|  | 10.5 |
|  | 16.7 |
|  | 21.4 |
| Form XXIV | 2.9 |
|  | 7.4 |
|  | 7.8 |
|  | 8.7 |
|  | 9.5 |
|  | 12.2 |
|  | 18.6 |
|  | 19.0 |
|  | 22.7 |
| Form XXV | 3.1 |
|  | 5.2 |
|  | 7.4 |
|  | 8.7 |
|  | 23.2 |
|  | 24.4 |
| Form XXVI | 3.7 |
|  | 8.4 |
|  | 9.0 |
|  | 17.1 |
|  | 18.7 |
|  | 20.1 |
|  | 23.0 |
| Form XXVII | 3.9 |
|  | 4.5 |
|  | 7.5 |
|  | 9.6 |
|  | 10.6 |

TABLE 13-continued

Forms XX, XXI, XXII, XXIII, XXIV, XXV, XXVI, XXVII, XXVIII, XXIX, and XXX

| Form | Degree 2θ |
|---|---|
|  | 13.0 |
|  | 15.3 |
|  | 18.7 |
| Form XXVIII | 7.6 |
|  | 9.5 |
|  | 12.2 |
|  | 16.5 |
|  | 17.0 |
|  | 18.0 |
|  | 21.5 |
|  | 22.3 |
| Form XXX | 9.0 |
|  | 9.7 |
|  | 12.0 |
|  | 16.5 |
|  | 17.0 |
|  | 21.6 |
|  | 22.5 |
|  | 24.3 |

Small Angle Powder X-Ray Diffraction

Methodology

Powder materials of different lots of atorvastatin calcium were packed in either glass or quartz x-ray capillaries with diameter of 1 to 2 mm. Small-Angle X-Ray Diffraction (SAXD) experiments were performed at the beamline ID2, European Synchrotron Radiation Facility (ESRF), Grenoble, France. The radiation wavelength was 0.996 Å (silicon channel-cut monochromator). The 2-dimensional SAXD images were recorded using image-intensified charge coupled device (CCD) detector and the data was expressed as reciprocal spacing q in $nm^{-1}$ units. The exposure time was adjusted to use the maximum dynamic of the detectors for every particular sample and was less than 1 s in the majority of cases. The 2-dimensional images were normalized to an absolute intensity scale after performing the standard detector corrections and azimuthally integrated to obtain the corresponding 1-dimensional x-ray diffraction curves. Peaks positions were measured using Gaussian fit using single peak analysis. The SAXD and (wide angle x-ray diffraction) WAXD q-scales were calibrated with silver behenate and silicon powders, respectively.

Table 14 shows the SAXRD peaks for Forms XX, XXII, XXIV, XXV, XXVII and XXX atorvastatin calcium.

TABLE 14

| SAXRD Data | |
|---|---|
| Form | Position of peaks, q, $nm^{-1}$ |
| XX | 2.11 |
|  | 3.93 |
| XXII | 2.85 |
|  | 3.48 |
|  | 4.16 |
| XXIV | 2.09 |
|  | 2.24 |
|  | 2.84 |
|  | 3.33 |
|  | 3.54 |
|  | 3.69 |
|  | 4.50 |
|  | 5.23 |

TABLE 14-continued

| SAXRD Data | |
|---|---|
| Form | Position of peaks, q, $nm^{-1}$ |
| XXV | 2.22 |
|  | 2.86 |
|  | 3.62 |
|  | 4.46 |
|  | 5.28 |
| XXVII | 2.19 |
|  | 2.76 |
|  | 2.86 |
|  | 3.27 |
|  | 3.33 |
|  | 4.00 |
|  | 4.69 |
|  | 4.97 |
| XXX | 2.13 |
|  | 4.26 |

Raman Spectroscopy

Methodology

The Raman spectrum was obtained on a Raman accessory interfaced to a Nicolet Magna 860 Fourier transform infrared spectrometer. The accessory utilizes an excitation wavelength of 1064 nm and approximately 0.45 W of neodymium-doped yttrium aluminum garnet (Nd:YAG) laser power. The spectrum represents 6 or 128 co-added scans acquired at 4 $cm^{-1}$ resolution. The sample was prepared for analysis by placing a portion into a 5-mm diameter glass tube and positioning this tube in the spectrometer. Peak tables were generated using the Nicolet software with default threshold and sensitivity settings. The spectrometer was calibrated (wavelength) with sulfur and cyclohexane at the time of use.

Table 15 shows the Raman spectra for Forms XX, XXII, XXIV, XXV, XXVII, and XXVIII atorvastatin calcium.

TABLE 15

| Raman Peak Listing Peak Positions in Wavenumbers ($cm^{-1}$) | |
|---|---|
| Form | $cm^{-1}$ |
| XX | 618 |
|  | 818 |
|  | 855 |
|  | 892 |
|  | 999 |
|  | 1034 |
|  | 1158 |
|  | 1178 |
|  | 1244 |
|  | 1412 |
|  | 1480 |
|  | 1528 |
|  | 1558 |
|  | 1604 |
|  | 1649 |
|  | 3059 |
| XXII | 618 |
|  | 820 |
|  | 855 |
|  | 998 |
|  | 1033 |
|  | 1157 |
|  | 1243 |
|  | 1364 |
|  | 1410 |
|  | 1526 |
|  | 1603 |

TABLE 15-continued

Raman Peak Listing
Peak Positions in Wavenumbers (cm$^{-1}$)

| Form | cm$^{-1}$ |
|---|---|
| | 1671 |
| | 3059 |
| XXIV | 133 |
| | 217 |
| | 247 |
| | 298 |
| | 422 |
| | 500 |
| | 617 |
| | 643 |
| | 697 |
| | 789 |
| | 811 |
| | 825 |
| | 857 |
| | 900 |
| | 925 |
| | 961 |
| | 1000 |
| | 1034 |
| | 1056 |
| | 1112 |
| | 1160 |
| | 1179 |
| | 1240 |
| | 1301 |
| | 1370 |
| | 1398 |
| | 1413 |
| | 1473 |
| | 1527 |
| | 1603 |
| | 1651 |
| | 2263 |
| | 2555 |
| | 2922 |
| | 2972 |
| | 3062 |
| XXV | 138 |
| | 224 |
| | 245 |
| | 300 |
| | 422 |
| | 495 |
| | 617 |
| | 644 |
| | 697 |
| | 726 |
| | 825 |
| | 859 |
| | 901 |
| | 1001 |
| | 1034 |
| | 1058 |
| | 1112 |
| | 1159 |
| | 1181 |
| | 1243 |
| | 1320 |
| | 1368 |
| | 1397 |
| | 1412 |
| | 1477 |
| | 1528 |
| | 1604 |
| | 1654 |
| | 2257 |
| | 2933 |
| | 3063 |
| XXVII | 130 |
| | 288 |
| | 366 |
| | 512 |
| | 581 |
| | 618 |
| | 634 |
| | 736 |
| | 821 |
| | 858 |
| | 898 |
| | 998 |
| | 1034 |
| | 1112 |
| | 1158 |
| | 1240 |
| | 1314 |
| | 1368 |
| | 1411 |
| | 1481 |
| | 1527 |
| | 1559 |
| | 1578 |
| | 1604 |
| | 1658 |
| | 2927 |
| | 3063 |
| XXVIII | 148 |
| | 248 |
| | 296 |
| | 341 |
| | 405 |
| | 522 |
| | 478 |
| | 617 |
| | 642 |
| | 699 |
| | 755 |
| | 824 |
| | 863 |
| | 999 |
| | 1034 |
| | 1062 |
| | 1090 |
| | 1159 |
| | 1180 |
| | 1242 |
| | 1298 |
| | 1316 |
| | 1369 |
| | 1412 |
| | 1468 |
| | 1525 |
| | 1603 |
| | 1640 |
| | 2882 |
| | 2940 |
| | 3060 |
| | 3376 |

Solid State Nuclear Magnetic Resonance (NMR)

Methodology

Solid-state $^{13}$C NMR and $^{19}$F NMR spectra were obtained at 293K on 500 MHz NMR spectrometer. Approximately 80 mg of sample were tightly packed into a 4 mm ZrO spinner for analysis. The one-dimensional solid state spectra were collected at ambient pressure and 293 K on a wide-bore Bruker-Biospin Avance DSX 500 MHz NMR spectrometer using a Bruker 4 mm HFX BL cross-polarization magic angle spinning (CPMAS) probe. To minimize the spinning side bands, spinning speed was set to 15.0 kHz, the maximum specified spinning speed for the 4 mm HFX BL probe. $^{13}$C CPMAS and $^{19}$F MAS peaks were peak-picked using Bruker-Biospin TOPSPIN 1.3 software, by suitably setting the spectral window and the peak picking threshold intensity to eliminate peak picking of spinning side bands. The detection sensitivity parameter (PC) was typically set to 0.5.

$^{13}$C CPMAS

The one-dimensional $^{13}$C spectra were collected using $^{1}$H-$^{13}$C cross-polarization magic angle spinning (CPMAS). To optimize the signal sensitivity, the cross-polarization contact time was adjusted to 2.3 ms, and the decoupling power was set to 80 kHz. The carbon spectra were acquired with approximately 1,100 scans with a recycle delay of 8 seconds. They were referenced using an external sample of adamantane, setting its upfield resonance to 29.5 ppm.

$^{19}$F MAS

The one-dimensional $^{19}$F spectra were collected using magic angle spinning (MAS) with proton decoupling. The decoupling field was set to approximately 65 kHz. $^{19}$F detected $^{1}$H T1 relaxation times were calculated based on inversion recovery experiments. For all samples, the probe background was reduced by subtracting signal from interleaved scans, during which a $^{19}$F presaturation pulse was applied. The spectra were acquired with approximately 64 scans with a recycle delay of 10 seconds. The samples were referenced using an external sample of trifluoroacetic acid (diluted to 50% V/V by H$_2$O), setting its resonance to −76.54 ppm.

Table 16 shows the $^{13}$C solid state NMR spectrum for Forms XX, XXII, XXIV, XXV, XXVII, XXVIII, and XXX atorvastatin calcium. Table 17 shows the $^{19}$F solid state NMR spectrum for Forms XX, XXII, XXIV, XXV, XXVII, XXVIII, and XXX atorvastatin calcium.

TABLE 16

CPMAS $^{13}$C Data

| Form | Solid State Chemical Shift$^a$ [ppm] |
|---|---|
| XX | 180.7 |
|  | 166.8 |
|  | 162.9 |
|  | 161.0 |
|  | 134.7 |
|  | 128.5 |
|  | 122.5 |
|  | 118.6 |
|  | 69.8 |
|  | 41.8 |
|  | 26.1 |
|  | 21.7 |
| XXII | 182.1 |
|  | 166.6 |
|  | 164.1 |
|  | 161.8 |
|  | 143.7 |
|  | 139.4 |
|  | 136.1 |
|  | 134.2 |
|  | 129.1 |
|  | 123.4 |
|  | 119.7 |
|  | 115.7 |
|  | 68.7 |
|  | 45.1 |
|  | 43.9 |
|  | 39.1 |
|  | 37.4 |
|  | 26.8 |
|  | 22.7 |
|  | 20.6 |
|  | 18.3 |
| XXIV | 187.5 |
|  | 185.2 |
|  | 184.2 |
|  | 180.5 |
|  | 179.0 |

TABLE 16-continued

CPMAS $^{13}$C Data

| Form | Solid State Chemical Shift$^a$ [ppm] |
|---|---|
|  | 178.4 |
|  | 177.4 |
|  | 166.8 |
|  | 162.7 |
|  | 160.9 |
|  | 138.7 |
|  | 136.2 |
|  | 133.7 |
|  | 128.7 |
|  | 124.4 |
|  | 122.4 |
|  | 121.2 |
|  | 120.5 |
|  | 118.0 |
|  | 115.7 |
|  | 69.8 |
|  | 67.4 |
|  | 65.7 |
|  | 46.4 |
|  | 44.3 |
|  | 43.5 |
|  | 40.6 |
|  | 26.7 |
|  | 25.5 |
|  | 21.8 |
|  | 19.6 |
|  | 0.0 |
| XXV | 186.3 |
|  | 185.0 |
|  | 182.5 |
|  | 177.0 |
|  | 167.0 |
|  | 166.2 |
|  | 162.8 |
|  | 160.9 |
|  | 138.6 |
|  | 136.1 |
|  | 133.4 |
|  | 129.2 |
|  | 128.5 |
|  | 126.0 |
|  | 124.0 |
|  | 121.5 |
|  | 120.7 |
|  | 118.0 |
|  | 116.8 |
|  | 116.0 |
|  | 69.9 |
|  | 68.0 |
|  | 46.4 |
|  | 43.3 |
|  | 40.9 |
|  | 25.7 |
|  | 25.2 |
|  | 21.3 |
|  | 20.0 |
|  | 0.6 |
| XXVII | 179.7 |
|  | 166.0 |
|  | 163.6 |
|  | 161.7 |
|  | 140.7 |
|  | 133.8 |
|  | 128.8 |
|  | 122.4 |
|  | 115.3 |
|  | 72.5 |
|  | 70.9 |
|  | 66.6 |
|  | 41.8 |
|  | 27.3 |
|  | 22.0 |
| XXVIII | 184.1 |
|  | 183.4 |
|  | 181.2 |
|  | 180.9 |

TABLE 16-continued

CPMAS $^{13}$C Data

| Form | Solid State Chemical Shift[a] [ppm] |
|---|---|
|  | 166.8 |
|  | 162.5 |
|  | 160.5 |
|  | 138.1 |
|  | 137.5 |
|  | 135.3 |
|  | 134.5 |
|  | 132.8 |
|  | 131.4 |
|  | 131.1 |
|  | 130.0 |
|  | 129.6 |
|  | 127.7 |
|  | 123.9 |
|  | 123.1 |
|  | 121.4 |
|  | 120.6 |
|  | 118.4 |
|  | 117.6 |
|  | 113.1 |
|  | 73.7 |
|  | 73.1 |
|  | 71.7 |
|  | 66.8 |
|  | 65.9 |
|  | 63.9 |
|  | 46.7 |
|  | 43.0 |
|  | 26.5 |
|  | 24.7 |
|  | 23.8 |
|  | 21.4 |
|  | 21.0 |
| XXX | 181.0 |
|  | 177.2 |
|  | 167.2 |
|  | 162.5 |
|  | 160.5 |
|  | 137.8 |
|  | 137.1 |
|  | 135.4 |
|  | 134.4 |
|  | 132.3 |
|  | 131.2 |
|  | 129.9 |
|  | 128.2 |
|  | 127.4 |
|  | 123.7 |
|  | 123.1 |
|  | 121.8 |
|  | 120.9 |
|  | 118.6 |
|  | 117.8 |
|  | 113.9 |
|  | 67.9 |
|  | 65.4 |
|  | 63.9 |
|  | 47.5 |
|  | 47.0 |
|  | 46.2 |
|  | 43.3 |
|  | 41.5 |
|  | 40.5 |
|  | 26.2 |
|  | 25.5 |
|  | 24.9 |
|  | 21.8 |
|  | 21.4 |

[a]Referenced using an external standard of crystalline adamantane, setting its upfield resonance to 29.5 ppm.

TABLE 17

MAS $^{19}$F Data

| Form | Fluorine chemical shift[a] [ppm] |
|---|---|
| XX | −113.9 |
| XXII | −112.0 |
|  | −114.8 |
|  | −118.9 |
| XXIV | −114.0 |
|  | −116.8 |
|  | −117.9 |
| XXV | −113.2 |
|  | −116.3 |
|  | −118.4 |
| XXVII | −112.2 |
|  | −113.0 |
|  | −117.2 |
| XXVIII | −116.4 |
|  | −117.1 |
|  | −119.2 |
| XXX | −116.7 |
|  | −118.6 |

[a]Referenced using an external sample of trifluoroacetic acid (diluted to 50% V/V by H$_2$O), setting its resonance to −76.54 ppm.

Additionally, Forms XXI, XXII, XXIII, XXIV, XXV, XXVI, XXVII, XXVIII, XXIX, and XXX atorvastatin calcium may be characterized by an x-ray powder diffraction and a solid state $^{19}$F nuclear magnetic resonance spectrum. For example:

A Form XXII atorvastatin calcium having an x-ray powder diffraction containing the following 2θ values measured using CuK$_a$ radiation: 10.0, 16.1, and 19.2, and a solid state $^{19}$F nuclear magnetic resonance having the following chemical shifts expressed in parts per million: −112.0, −114.8, and −118.9.

A Form XXIV atorvastatin calcium having an X-ray powder diffraction containing the following 2θ values measured using CuK$_a$ radiation: 7.4, 9.5 and 12.2, and a solid state $^{19}$F nuclear magnetic resonance having the following chemical shifts expressed in parts per million: −114.0, −116.8, and −117.9.

A Form XXV atorvastatin calcium having an x-ray powder diffraction containing the following 2θ values measured using CuK$_a$ radiation: 7.4, 8.7, 19.2, and 20.0, and a solid state $^{19}$F nuclear magnetic resonance having the following chemical shifts expressed in parts per million: −113.2, −116.3, and −118.4.

A Form XXVII atorvastatin calcium having an x-ray powder diffraction containing the following 2θ values measured using CuK$_a$ radiation: 3.9, 7.5, and 18.7, and a solid state $^{19}$F nuclear magnetic resonance having the following chemical shifts expressed in parts per million: −112.2, −113.0, and −117.2.

A Form XXVIII atorvastatin calcium having an x-ray powder diffraction containing the following 2θ values measured using CuK$_a$ radiation: 7.6, 9.5, 20.5, and 22.3, and a solid state $^{19}$F nuclear magnetic resonance having the following chemical shifts expressed in parts per million: −116.4, −117.1, and −119.2.

A Form XXX atorvastatin calcium having an x-ray powder diffraction containing the following 2θ values measured using CuK$_a$ radiation: 3.1, 9.0, and 21.6, and a solid state $^{19}$F nuclear magnetic resonance having the following chemical shifts expressed in parts per million: −116.7 and −118.6.

The forms of atorvastatin calcium described in the present invention may exist in anhydrous forms as well as containing various amounts of water and/or solvents. In general, these forms are equivalent to the anhydrous forms and are intended to be encompassed within the scope of the present invention.

The forms of atorvastatin calcium of the present invention, regardless of the extent of water and/or solvent having equivalent x-ray powder diffractograms are within the scope of the present invention.

The new forms of atorvastatin calcium described in the present application have advantageous properties.

The ability of a material to form good tablets at commercial scale depends upon a variety of physical properties of the drug, such as, for example, the Tableting Indices described in Hiestand H. and Smith D., Indices of Tableting Performance, Powder Technology, 1984, 38; 145-159. These indices may be used to identify forms of atorvastatin calcium which have superior tableting performance. One such index is the Brittle Fracture Index (BFI), which reflects brittleness, and ranges from 0 (good-low brittleness) to 1 (poor—high brittleness).

The present invention provides a process for the preparation of Forms XX, XXI, XXII, XXIII, XXIV, XXV, XXVI, XXVII, XXVIII, XXIX, and XXX atorvastatin calcium which comprises forming atorvastatin calcium from a solution or slurry in solvents under conditions which yield Forms XX, XXI, XXII, XXIII, XXIV, XXV, XXVI, XXVII, XXVIII, XXIX, and XXX atorvastatin calcium.

The precise conditions under which Forms XX, XXI, XXII, XXIII, XXIV, XXV, XXVI, XXVII, XXVIII, XXIX, and XXX atorvastatin calcium are formed may be empirically determined, and it is only possible to give a number of methods which have been found to be suitable in practice.

The compounds of the present invention can be prepared and administered in a wide variety of oral and parenteral dosage forms. Thus, the compounds of the present invention can be administered by injection, that is, intravenously, intramuscularly, intracutaneously, subcutaneously, intraduodenally, or intraperitoneally. Also, the compounds of the present invention can be administered by inhalation, for example, intranasally. Additionally, the compounds of the present invention can be administered transdermally. It will be obvious to those skilled in the art that the following dosage forms may comprise as the active component a compound of the present invention.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, solubilizers, lubricants, suspending agents, binders, preservatives, tablet disintegrating agents, or an encapsulation material.

In powders, the carrier is a finely divided solid which is in a mixture with the finely divided active component.

In tablets, the active component is mixed with the carrier having the necessary binding properties in suitable proportions and compacted in the shape and size desired.

The powders and tablets preferably contain from two or ten to about seventy percent of the active compound. Suitable carriers are magnesium carbonate, methylcellulose, sodium carboxymethylcellulose, a low melting wax, cocoa butter, and the like. The term 'preparation' is intended to include the formulation of the active compound with encapsulating material as a carrier providing a capsule in which the active component, with or without other carriers, is surrounded by a carrier, which is thus in association with it.

Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, retention enemas, and emulsions, for example water or water propylene glycol solutions. For parenteral injection, liquid preparations can be formulated in solution in aqueous polyethylene glycol solution.

Aqueous solutions suitable for oral use can be prepared by dissolving the active component in water and adding suitable colorants, flavors, stabilizing and thickening agents, as desired.

Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dosage preparation may be varied or adjusted from 0.5 mg to 100 mg, preferably 2.5 to 80 mg according to the particular application and the potency of the active component. The composition can, if desired, also contain other compatible therapeutic agents.

In therapeutic use as hypolipidemic and/or hypocholesterolemic agents and agents to treat BPH, osteoporosis, and Alzheimer's disease, the Forms XX, XXI, XXII, XXIII, XXIV, XXV, XXVI, XXVII, XXVIII, XXIX, and XXX atorvastatin calcium utilized in the pharmaceutical method of this invention are administered at the initial dosage of about 2.5 mg to about 80 mg daily. A daily dose range of about 2.5 mg to about 20 mg is preferred. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstance is reached. For convenience, the total daily dosage may be divided and administered in portions during the day if desired.

The following nonlimiting examples illustrate the inventors' preferred methods for preparing the compounds of the invention:

Example 1

[R—(R*,R*)]-2-(4-fluorophenyl)-β,δ-dihydroxy-5-(1-methylethyl)-3-phenyl-4-[(phenylamino)carbonyl]-1H-pyrrole-1-heptanoic Acid Hemi Calcium Salt (Forms XX, XXI, XXII, XXIII, XXIV, XXV, XXVI, XXVII, XXVIII, XXIX, and XXX Atorvastatin Calcium)

Form XX Atorvastatin Calcium
Method A

A 12.2 g sample of Form I atorvastatin calcium (U.S. Pat. No. 5,969,156, which is herein incorporated by reference) was suspended in 300 mL of methanol (MeOH):$H_2O$ (95:5, v:v) and sonicated. The resulting suspension was filtered into a 1 L flask. The sample was evaporated on a rotary evaporator with an unheated water bath and the vacuum provided with an aspirator. The solid obtained was dried under vacuum at ambient temperature overnight to afford Form XX atorvastatin calcium.
Method B A 24 mg sample of Form I atorvastatin calcium (U.S. Pat. No. 5,969,156) was dissolved in 7 mL of ethanol (EtOH):$H_2O$ (4:1, v:v) and filtered through a 0.2 μm nylon filter. The resulting solution was evaporated in an open vial to dryness to afford Form XX atorvastatin calcium.

Form XXI Atorvastatin Calcium
Method A

A 3.6 g sample of Form I atorvastatin calcium (U.S. Pat. No. 5,969,156) was dissolved in 10 mL of tetrahydrofuran:water (9:1, v/v) at 43° C. A 1-mL aliquot was filtered into a vial and approximately 1 mL of pre-warmed acetonitrile (ACN) was added drop-wise. The clear solution was placed in a refrigerator. Solids formed within 1 day, recovered with vacuum filtration, and air-dried at ambient temperature to afford Form XXI atorvastatin calcium.
Method B A 10.5 g sample of Form I (U.S. Pat. No. 5,969,156) was slurried in 450 mL of isopropyl alcohol (IPA)/50 mL $H_2O$ (9:1) at room temperature for 20 days. The sample was then vacuum filtered. The sample was then slurried in 450 mL of ACN/50 mL $H_2O$ (9:1) overnight. The sample was vacuum filtered for 5 hours to afford Form XXI atorvastatin calcium.

Form XXII Atorvastatin Calcium

An 11.5 g sample of Form XX atorvastatin calcium (prepared as described above) was mixed with 29 mL of MeOH and stirred on an ambient temperature orbital shaker for 1 day. The sample was then vacuum dried at ambient temperature for 1 day. The recovered solid was mixed with 29 mL of MeOH and slurried on an ambient temperature orbital shaker for less than 1 hour. The gel that formed was then mixed with an additional 40 mL of MeOH and slurried on the ambient temperature orbital shaker for 3 days. The solids were vacuum dried at ambient temperature for 1 day to afford Form XXII atorvastatin calcium.

Form XXIII Atorvastatin Calcium
Method A

A 1.5 g sample of Form I atorvastatin calcium (U.S. Pat. No. 5,969,156) was slurried with approximately 75 mL of ACN:water (9:1, v/v) in a flask and placed on an ambient temperature orbital shaker block for 1 day. The sample was divided into four portions and centrifuged and the supernatant decanted and discarded. The recovered solids were returned to the shaker block for 1 hour. The samples were air dried for less than 1 day. The four portions were recombined and the sample was further air-dried at ambient conditions for 3 hours to afford Form XXIII atorvastatin calcium.

Method B

An 11.0 g sample of Form I atorvastatin calcium (U.S. Pat. No. 5,969,156) was slurried with approximately 430 mL of ACN:water (9:1, v/v) on an ambient temperature magnetic stir plate at 500 rpm for 2 days. The sample was vacuum filtered through a 0.22-μm nylon membrane filter and the filtered solids were air dried at ambient conditions for 1 day to afford Form XXIII atorvastatin calcium.

Form XXIV Atorvastatin Calcium

A 1.0 g sample containing a mixture of amorphous atorvastatin calcium (U.S. Pat. No. 6,087,511, which is herein incorporated by reference) and Form XX atorvastatin calcium (prepared as described above) was slurried with 195 mL of ACN:water (9:1, v/v) in a flask and placed on a magnetic stir plate set at 55° C. and 500 rpm for 1 day. The sample was vacuum filtered using a 0.22-μm nylon membrane filter and the solids were slurried with 195 mL of the fresh solvent at the same conditions for 1 day. Again, the sample was vacuum filtered using 0.22-μm nylon membrane filter and the solids were slurried with 195 mL of the fresh solvent at the same conditions for 1 day. The solids were isolated by vacuum filtration and were air dried in a petri dish at ambient conditions for 4 days to afford Form XXIV atorvastatin calcium.

Form XXV Atorvastatin Calcium

A 58 mg sample of Form XX atorvastatin calcium (prepared as described above) was slurried in 2 mL of ACN:water (9:1) on a magnetic stir plate for 5 days and then filtered to afford Form XXV atorvastatin calcium.

Form XXVI Atorvastatin Calcium
Method A

A 2.0 g sample of Form I atorvastatin calcium (U.S. Pat. No. 5,969,156) was slurried with 0.57 mL of water in a vial, 5.1 mL of MeOH added, and the sample was placed on an orbital shaker block at 58 to 60° C. for 3 days. The resulting sample was vacuum dried between 70-75° C. for 3 days to afford Form XXVI atorvastatin calcium.
Method B A 5.0 g sample of Form I atorvastatin calcium (U.S. Pat. No. 5,969,156) was dissolved in 200 mL of 80:20 (v/v) water/MeOH at 60° C. After forming a solution, a slurry resulted while stirring at 60° C. The slurry was isolated via vacuum filtration after 2.5 hours. The material was vacuum dried at 45° C. overnight to afford Form XXVI atorvastatin calcium.

Form XXVII Atorvastatin Calcium
Method A

A sample of Form VIII atorvastatin calcium (U.S. Pat. No. 6,605,729, which is herein incorporated by reference) was heated on a sample holder in a Variable Temperature X-ray powder diffraction unit at 5° C./minute ramp rate. The temperature was held at 35°, 80°, 100°, 115°, and 140° C. for approximately 15 minutes before reaching 165° C. to afford Form XXVII atorvastatin calcium. The Form XXVII atorvastatin calcium remained unchanged upon cooling to 40° C.

Method B

A sample of Form VIII atorvastatin calcium (U.S. Pat. No. 6,605,729) was heated using a variable temperature XRPD with humidity conditions remaining uncontrolled throughout the experiment. The sample was heated in a series of 4 steps beginning at 35° C. It continued up to 135° C. (holding for 13.5 min) and then on to 148° C. (holding for 15.5 min) before returning to 35° C. (holding for 15.5 min) to afford Form XXVII atorvastatin calcium. Form XXVII atorvastatin calcium was obtained at 148° C. and remained unchanged upon cooling to 35° C.

Form XXVIII Atorvastatin Calcium

A 0.3 g sample of amorphous atorvastatin calcium (U.S. Pat. No. 6,087,511) was slurried with 1 mL of ethylene glycol at 50° C. for 24 hours. The solids were isolated by vacuum filtration at ambient conditions to afford Form XXVIII atorvastatin calcium.

Form XXIX Atorvastatin Calcium

A 1.0 g sample of amorphous atorvastatin calcium (U.S. Pat. No. 6,087,511) was slurried with 8 mL of water:tetrahydrofuran (4:1, v/v) at ambient temperature. The mixture was seeded with atorvastatin calcium Form XII (U.S. Pat. No. 6,605,729) and stirred at ambient conditions for 5 hours. The solids were isolated by vacuum filtration to afford Form XXIX atorvastatin calcium.

Form XXX Atorvastatin Calcium

Method A

A slurry containing 3.0 g of amorphous atorvastatin calcium (U.S. Pat. No. 6,087,511) and 24 mL of ethylene glycol was shaken on an ambient temperature orbital shaker block for about 1 day. The slurry was vacuum filtered and the solids were air dried at ambient temperature for 6 days to afford Form XXX atorvastatin calcium.

Method B

A 200 mg sample of Form I atorvastatin calcium (U.S. Pat. No. 5,969,156) was exposed to ACN vapor at ambient temperature inside a sealed chamber for two months to afford Form XXX atorvastatin calcium.

The invention claimed is:

1. A Form XXIII atorvastatin calcium having an X-ray powder diffraction containing the following 2θ values measured using CuKa radiation: 4.1, 5.0, 6.3, 7.7, 8.5, 9.1, 10.5, 16.7, 18.4, 20.2, and 21.4.

2. A Form XXIII atorvastatin calcium having an X-ray powder diffraction containing the following 2θ values measured using CuKa radiation: 3.2, 4.1, 5.0, 6.3, 7.2, 7.7, 8.1, 8.5, 9.1, 10.1, 10.5, 12.1, 12.8, 13.3, 16.7, 18.4, 19.1, 20.2, 21.0, 21.4, 23.2, 24.3, 25.2, and 29.3.

3. A Form XXIII atorvastatin calcium having an X-ray powder diffraction containing the following 2θ values measured using CuKa radiation: 4.1, 5.0, 6.3, 7.7, 8.5, 9.1, 10.5, 16.7, and 21.4.

* * * * *